US006777204B1

(12) United States Patent
Takahashi et al.

(10) Patent No.: US 6,777,204 B1
(45) Date of Patent: Aug. 17, 2004

(54) RECEPTOR PROTEIN AND METHOD FOR DIAGNOSING INFLAMMATORY DISEASES BY USING THE SAME

(75) Inventors: Tsuneo Takahashi, Tokyo (JP); Mitsuharu Ono, Shizuoka-Ken (JP); Hiroshi Ishimaru, Kanagawa-Ken (JP); Kimiyoshi Kanno, Shizuoka-Ken (JP); Chiaki Takahashi, Shizuoka-Ken (JP)

(73) Assignee: Asahi Kasei Kabushiki Kaisha, Osaka (JP)

(*) Notice: Subject to any disclaimer, the term of this patent is extended or adjusted under 35 U.S.C. 154(b) by 0 days.

(21) Appl. No.: 09/786,442

(22) PCT Filed: Sep. 3, 1999

(86) PCT No.: PCT/JP99/04801

§ 371 (c)(1),
(2), (4) Date: Mar. 5, 2001

(87) PCT Pub. No.: WO00/14229

PCT Pub. Date: Mar. 16, 2000

(30) Foreign Application Priority Data

Sep. 3, 1998 (JP) ............................................ 10-249752
Mar. 16, 1999 (JP) ............................................ 11-070800

(51) Int. Cl.[7] ............................ C12P 21/06; C07K 1/00; A61K 38/00; C12N 15/74; C07H 21/04
(52) U.S. Cl. ................ 435/69.1; 435/252.3; 435/320.1; 435/325; 435/471; 536/23.5; 530/300; 530/350
(58) Field of Search ................................. 530/350, 300; 435/69.1, 252.3, 320.1, 325, 471, 761, 71.1, 71.2, 771; 536/23.5

(56) References Cited

U.S. PATENT DOCUMENTS 5,508,384 A 4/1996 Murphy et al.
5,861,272 A * 1/1999 Li et al.

FOREIGN PATENT DOCUMENTS

WO    WO 94/01548    * 1/1994

OTHER PUBLICATIONS

Alvarez V, et al. Immunogenetics 44(6):446–452, 1996.*
Lamerdin JE et al. Database GenEmbl. Accession No. AC005387. Aug. 8, 1998.*
Partanen JM. Database GenEmbl. Accession No. HSF-GFR4. May 15, 1991.*
Database EMBL Homo sapiens chromosome 19 clone CRD–3023J11, Joint Genone Institute Stanford Human Genome Center, 1999, XP002216707.
S. Zhao et al., "Use of BAC End sequences from library RPCI–11 for sequence–redy building," Database EMBL RPCI–11–381D11.TJ RPCI–11 H. sapiens genomic clo, 1999, XP002216708.
Sornasse et al., "Antigen–pulsed Dendritic Cells Can Efficiently Induce an Antibody Response In Vivo", J. Exp. Med., vol. 175, 1992, pp. 15–21.

Mehta–Damani et al., "Generation of Antigen–Specific CD8[+] CTLs for Naive Precursors", J. Immunol., vol. 153, 1994, pp. 996–1003.
Barclay et al., "Leucocyte Antigen Facts Book", Academic Press Inc., 1993, pp. 38–87.
Hisashi Iizasa and Kouji Matsushima, "Rinsho Men–eki (Clinical Immunology)", vol. 28, 1996, pp. 731–737.
Howard et al., "Chemokines: progress toward identifying molecular targets for therapeutic agents", TIBTECH, vol. 14, 1996, pp. 46–51.
Power et al., "Cloning and characterization of human chemokine receptors", Trends Pharmacol. Sci., vol. 17, 1996, pp. 209–213.
Marleau et al., "Human RANTES Acts as a Receptor Antagonist for Guinea Pig Eotaxin In Vitro and In Vivo", J. Immunol., vol. 157, 1996, pp. 4141–4146.
Choe et al., The β–Chemokine Receptors CCR3 and CCR5 Facilitate Infection by Primary HIV–1 Isolates, vol. 85, 1996, pp. 1135–1148.
Bleul et al., "The lymphocyte chemoattractant SDF–1 is a ligand for LESTR/fusin and blocks HIV–1 entry", Nature, vol. 382, 1996, pp. 829–833.
Premack et al., "Chemokine receptors: Gateways to inflammation and infection", Nature Med., vol. 2, No. 11, 1996, pp. 1174–1178.
Loetscher et al., "Chemokine Receptor Specific for IP10 and Mig: Structure, Function, and Expression in Activated T–Lymphocytes", J. Exp. Med., vol. 184, 1996, pp. 963–969.
Samson et al., "ChemR23, a putative chemoattractant receptor, is expressed in monocyte–derived dendritic cells and macrophages and is a coreceptor for SIV and some primary HIV–1 strains", Eur. J. Immunol., vol. 28, 1998, pp. 1689–1700.

(List continued on next page.)

Primary Examiner—Robert Landsman
(74) Attorney, Agent, or Firm—Young & Thompson

(57) ABSTRACT

Disclosed are a novel seven-pass transmembrane receptor protein found in immature dendritic cells and a DNA encoding the same. Further, disclosed are a replicable recombinant DNA which comprises a replicable expression vector and, operably inserted therein, the above-mentioned DNA; a cell of a microorganism or cell culture (transformant), which is transformed with the above-mentioned replicable recombinant DNA; a seven-pass transmembrane receptor protein which is produced on the cell surface of the above-mentioned transformant; a method for screening a ligand which binds to the above-mentioned seven-pass transmembrane receptor protein, and a method for screening a substance which inhibits the ligand from binding to the seven-pass transmembrane receptor protein; and an antibody which binds to the above-mentioned seven-pass transmembrane receptor protein. The present invention also discloses a method for the diagnosis of an inflammatory disease, such as rheumatism, which comprises determining the amount of the seven-pass transmembrane receptor protein expressed in human leukocytes.

5 Claims, 3 Drawing Sheets

OTHER PUBLICATIONS

Loetscher et al., "CCR5 is characteristic of Th1 lymphocytes", vol. 391, 1998, pp. 344–345.

Bonecchi et al., "Differential Expression of Chemokine Receptors and Chemotactic Responsiveness of Type 1 T Helper Cells (Th1s) and Th2s", J. Exp. Med., vol. 187, No. 1, 1998, pp. 124–134.

Smyth, "Therapy of rheumatoid arthritis", vol. 51, No. 6, 1972, pp. 31–39.

Arnett et al., "The American Rheumatism Association 1987 Revised Criteria for the Classification of Rheumatoid Arthritis", Arthritis Rheum., vol. 31, No. 3, 1988, pp. 315–324.

Yamamae, "Igaku no ayumi (Progress in Medicine)", vol. 182, No. 9, 1997, pp. 605–610.

Lisitsyn et al., "Cloning the Differences Between Two Complex Genomes", Science, vol. 259, 1993, pp. 946–951.

Romani et al., "Proliferating Dendritic Cell Progenitors in Human Blood", J. Exp. Med., vol. 180, 1994, pp. 83–93.

Talmor et al., Eur. J. Immunol., vol. 28, 1998, pp. 811–817.

Morse et al., "Generation of Dendritic Cells in Vitro From Peripheral Blood Mononuclear Cells with Granulocyte Macrophage– Colony–Stimulating Factor, Interleukin–4, and Tumor Necrosis Factor–α for Use in Cancer Immunotherapy", Ann Surg., vol. 226, 1997, pp. 6–16.

Kroll et al., "Functional expression of a human C5a receptor clone in *Xenopus oocytes* requires additional RNA", FEBS lett., vol. 291, 1991, pp. 208–210.

Kyte et al., "A Simple Method for Displaying the Hydropathic Character of a Protein", J. Mol. Biol., vol. 157, 1982, pp. 105–132.

Crass et al., "Expression cloning of the human C3a anaphylatoxin receptor (C3aR) from differentiated U–937 cells", Eur. J. Immunol., vol. 26, 1996, pp. 1944–1950.

Boulay et al., "Synthesis and Use of a Novel N–formyl Peptide Derivative to Isolate a Human N–Formyla Peptide Receptor cDNA", Biochem. Biophys. Res. Commun., vol. 168, No. 3, 1990, pp. 1103–1109.

Combadiere et al., "Cloning and Functional Expression of a Human Eosinophil CC Chemokine Receptor", J. Biol. Chem., vol. 270, No. 27, 1995, pp. 16491–16494.

Collins et al., "Cosmids" A type of plasmid gene–cloning vector that is packageable in vitro in bacteriophage λ heads, Proc. Natl. Acad. Sci., vol. 75, No. 9, 1978, pp. 4242–4246.

Samson et al., "Molecular Cloning and Functional Expression of a New Human CC–Chemokine Receptor Gene", Biochemistry, vol. 35, 1996, pp. 3362–3367.

Kenichi Kasai, "Tanpakushitsu, Kakusan, Kouso (Protein, Nucleic Acid and Enzyme)", vol. 37, 1992, pp. 2977–2984.

Whyte et al., "Impairment of Function in Aging Neutrophils is Associated with Apoptosis", J. Immunol., vol., 150, Nov. 11, 1993, pp. 5124–5134.

Watson et al., "Neutrophil Apoptosis Is Modulated by Endothelial Transmigration and Adhesion Molecule Engagement", J. Immunol., vol. 158, 1997, pp. 945–953.

Gray et al., "CD97 is a Processed, Seven–Transmembrane, Heterodimeric Receptor Associated with Inflammation", J. Immunol., vol. 157, 1996, pp. 5438–5447.

Alvarez et al., "Molecular evolution of the N–formyl peptide and C5a receptors in non–human primates", Immunogenetics, vol. 44, 1996, pp. 446–452.

Boulay et al., "Expression Cloning of a Receptor for C5a Anaphylatoxin on Differentiated HL–60 Cells", Biochemistry, vol. 30, 1991, pp. 2993–2999.

Perret et al., "Cloning and functional expression of the canine anaphylatoxin C5a receptor", Biochem. J., vol. 288, 1992, pp. 911–971.

Gerard et al., "The chemotactic receptor for human C5a anaphylatoxin", Nature, vol. 349, 1991, pp. 614–617.

Ohno et al., "A putative chemoattractant receptor, C5L2, is expressed in granulocyte and immature dendritic cells, but not in mature dendritic cells", Molecular Immunology, vol. 37, 2000, pp. 407–412.

\* cited by examiner (a)

(b)

Storage time after collection of blood (H)

RECEPTOR PROTEIN AND METHOD FOR DIAGNOSING INFLAMMATORY DISEASES BY USING THE SAME

This application is a 371 application of PCT/JP99/04801 filed on Sep. 3, 1999.

BACKGROUND OF THE INVENTION

1. Field of the Invention

The present invention relates to a novel seven-pass transmembrane receptor protein found in immature dendritic cells and a DNA encoding the same. More particularly, the present invention is concerned with a human seven-pass transmembrane receptor protein having the amino acid sequence of SEQ ID NO:2 and a DNA encoding the same. By the use of the seven-pass transmembrane receptor protein and the DNA encoding the same which are provided according to the present invention, it has become possible to screen a substance which can be used for treating or preventing diseases mediated by the functions of dendritic cells, and to provide a method and a reagent for the diagnosis of such diseases. Also, the present invention is concerned with a replicable recombinant DNA which comprises a replicable expression vector and, operably inserted therein, the above-mentioned DNA; a cell of a microorganism or cell culture (transformant), which is transformed with the above-mentioned replicable recombinant DNA; a seven-pass transmembrane receptor protein which is produced on the cell surface of the above-mentioned transformant; a method for screening a ligand which binds to the above-mentioned seven-pass transmembrane receptor protein, and a method for screening a substance which inhibits the ligand from binding to the seven-pass transmembrane receptor protein; and an antibody which binds to the above-mentioned seven-pass transmembrane receptor protein. The present invention is also concerned with a method for the diagnosis of an inflammatory disease, which comprises determining the amount of the seven-pass transmembrane receptor protein expressed in human leukocytes.

2. Prior Art

When the living body of an organism suffers a disorder, such as an infection or inflammation, the cells at the site of the disorder release various protein factors, thereby transmitting the information of the disorder to the cells participating in the biological defense mechanism. In the case of infections, leukocytes, especially granulocytes (for example, neutrophils) and macrophages, have the function to trigger the biological defense mechanism. Like the granulocytes, dendritic cells (i.e., star-shaped cells having outwardly extending dendrites wherein the star-shaped cells are found in lymph nodes and germinal centers) are derived from myeloid hematopoietic stem cells, and play an important role in immunity and inflammation, especially in antigen presentation.

A macrophage is one type of the antigen presenting cells and it presents an antigen to activated T and B cells (Sornasse et al., J. Exp. Med., 175, 15–21, 1992). However, the activation of helper T cells depends on the antigen presentation by the dendritic cells. It is considered that the dendritic cells capture antigens in peripheral blood, and move to lymph, and mature in lymph nodes. It has been reported that both macrophages and dendritic cells at any stage of maturation can present an antigen to the activated T cells; however, only matured dendritic cells can sensitize naive T cells (Mehta-Damani et al., J. Immunology, 153, 996–1003, 1994). Dendritic cells are derived from hematopoietic stem cells, but precursor dendritic cells and immature dendritic cells are found in blood and lymph, and fully matured dendritic cells are found in spleen and lymph nodes. In general, the immature dendritic cells have the high ability to take in an antigen, and the higher the degree of the maturation of the dendritic cells, the higher their ability to perform antigen presentation becomes. The dendritic cells presenting an antigen express large amounts of MHC (Major Histocompatibility Complex) class I proteins and class II proteins.

As described above, the dendritic cells participate in immunity and inflammation in the living body and serve to protect the living body by a beneficial immune response. However, in some cases, the dendritic cells also cause an undesirable immune response (such as an autoimmune response) and an undesirable inflammatory reaction. Therefore, it is considered that if a method for regulating the functions of the dendritic cells can be found out, it will become possible to treat infections and tumors by causing a beneficial immune response and to treat autoimmune diseases and the like by suppressing an adverse immune response.

The functions of the dendritic cells, such as proliferation, differentiation, activation and chemotaxis, are regulated by various receptor proteins expressed by the dendritic cells. A receptor is a protein which is present on the surface of a cell and which binds, with high affinity, to a specific substance (a signaling molecule) which is found on the surface of another cell or in body fluid. When the signaling molecule binds to the receptor, the binding (which is an extracellular event) is converted by the receptor into an intracellular signal to thereby cause a cellular response (Alberts, Bruce et al. eds., "Molecular Biology of the Cell", 2nd ed., Garland Publishing, Inc., pp. 681–726, 1989). The substance which binds to a receptor is generally called a "ligand". It is conceived that a substance which affects the functions of a receptor expressed by the dendritic cells can be used for negative or positive regulation of the dendritic cell functions thereby treating diseases caused by excess functioning or insufficient functioning of the dendritic cells. Examples of substances which affect the functions of a receptor expressed by the dendritic cells include a substance which binds to the receptor to thereby stimulate the cells, a substance which binds to the receptor to thereby inhibit the receptor from being stimulated by other ligands, and a substance which binds to the receptor to thereby inhibit a stimulation by other ligands from being transduced into the cell.

Examples of various receptors known in the art include cytokine receptors, EGF (Epidermal Growth Factor) receptors and seven-pass transmembrane receptors ("The Leukocyte Antigen Facts Book", Academic Press Inc., 38–49, 1993), and the functions of these receptors are diverse. A seven-pass transmembrane receptor, which is one of the above-mentioned receptors, is also called a "G-protein coupled receptor (GPCR)" or a "rhodopsin-type receptor". Studies on the seven-pass transmembrane receptors have begun only recently, and it is believed that a large number of still unknown seven-pass transmembrane receptors exist.

An explanation is made below taking leukocytes as an example. Examples of receptors which have been identified as the seven-pass transmembrane receptors present in leukocytes include receptors which bind to anaphylatoxins, receptors which bind to chemokines and receptors which bind to PAF (Platelet-Activating Factor). An anaphylatoxin receptor participates in the functions of neutrophils and macrophages, such as the production of active oxygen, chemotaxis and activation of cell adhesion (Bouley, F. et al., Biochemistry, 30, 2993–2999, 1991). Further, the below-described observation has been reported in connection with IL-8 (Interleukin 8) receptor, which is one of chemokine receptors. When an inflammation inducer is intra-abdominally administered to a mouse deficient in a homologue of IL-8 (Interleukin 8) receptor, various phenomena are observed, such as a decrease in neutrophil infiltration, an onset of neutrophilia (phenomenon wherein activation and proliferation of neutrophils occur, but infiltration by neutrophils does not take place), and an increase in granulocytes and plasma cells in bone marrow and lymph nodes (Hisashi IIZASA and Kouji MATSUSHIMA, "Rinsho Men-eki (Clinical Immunology)", 28, 731–737, 1996). Among the substances which act on the receptors, the substances which are considered to have the possibility of being useful as pharmaceuticals include substances (such as IL-8 and MCP-1 (Monocyte Chemotactic Protein 1)) which bind to the receptors to thereby stimulate cells, and the substances (such as IL-8 mutants) which bind to the receptors to thereby inhibit the receptors from being stimulated by other ligands (Howard, O. M. Z et al., TIBTECH, 14, 46–51, 1996). However, in many cases, a single receptor binds to any of a plurality of signaling molecules, and a single signaling molecule binds to any of a plurality of receptors. Therefore, for developing a treatment for a disease, knowledge of only signaling molecules participating in the disease is insufficient. For example, fourteen different receptors are known to bind to the same signaling molecule called serotonin. These fourteen different receptors for serotonin include not only seven-pass transmembrane receptors, but also an ion channel-type receptor having a signal transduction pathway which is completely different from those of the seven-pass transmembrane receptors. In addition, with respect to each of the fourteen receptors, a compound which specifically binds thereto is known (1996 Receptor & Ion Channel Nomenclature, Supplement 1–81 Trends Pharmacol. Sci., 1996), and, therefore, studies have been made for individually using these receptors for the treatment of different diseases. Further, in the case of chemokines, it is well known in the art that a single signaling molecule (one type of chemokine) reacts with any of a number of different receptors and, at the same time, a single receptor reacts with any of a number of different signaling molecules (different types of chemokines) (Power, C. A. et al., Trends Pharmacol. Sci., 17, 209–213, 1996).

As apparent from the above, even when a disease is caused by a single signaling molecule, the signaling molecule binds to any of a number of different receptors which are present on different types of cells. Therefore, for specifically regulating the functions of a specific type of cell which is causative of the disease, it is important to specify the receptor which is expressed on the cell rather than specifying the signaling molecule which acts on the cell. For example, in the case of a chemokine (which is one of signaling molecules), no single type of leukocyte which reacts with the signaling molecule RANTES (Regulated on Activation, Normal T cell Expressed and Secreted) can be specified because there are different types of leukocytes which are reactive with RANTES. On the other hand, eosinophils (one type of leukocytes) specifically express the chemokine receptor CCR3 (C—C Chemokine Receptor 3), and, hence, a method for specifically regulating eosinophils can be searched for by using the receptor CCR3 (Howard, O. M. Z. et al., TIBTECH, 14, 46–51, 1996).

The human receptors and the receptors in other species are known to exhibit different reactions with m the same compound (see, for example, Marleau, S. et al., J. Immunol. 157, 4141–4146, 1996). For example, some substances which activate the human receptors are known to inhibit the activation of the receptors in other species. Further, some receptors are known to act as a receptor for viruses during viral infection (see, for example, Choe, H. et al., Cell 85, 1135–1148, 1996), and it is also known that a molecule which binds to such a receptor prevents the viral infection (see, for example, Bleul, C. C. et al., Nature, 382, 829–833, 1996). In this case, it is important to identify the receptor expressed by the cells wherein the receptor is used by the viruses for infection. It is also known that specific types of viruses can complete infection only when the virus binds to a receptor in a specific species.

There are signaling molecules (e.g., PF4 and HCC1 which are chemokines) which are presumed to bind to receptors which are seven-pass transmembrane receptors, wherein, however, the receptors have not yet been identified (Premack, B. A. et al., Nature Medicine, 2, 1174–1178, 1996; and Loetscher, M. et al., J. Exp. Med., 184, 963–969, 1996). Especially, with respect to the chemokines, a number of still unknown chemokines are presumed to exist (Howard, O. M. Z. et al., TIBTECH, 14, 46–51, 1996), and, therefore, a number of receptors which bind to the unknown chemokines are also expected to exist.

As in the case of the leukocytes described above, not all of the receptors for the molecules which act on the dendritic cells have been found out, and a number of seven-pass transmembrane receptors are expected to exist on the dendritic cells. As an example of seven-pass transmembrane receptors present on mature dendritic cells, ChemR23 has been reported (Samson, M. et al., Eur. J. Immunol., 28, 1689–1700, 1998). A method for regulating the functions of dendritic cells and ultimately for regulating diseases can be established when it becomes possible to obtain various receptors expressed in the dendritic cells at different stages of differentiation and to obtain substances which affect the functions of each of the obtained various receptors.

With respect to the endogenous substances which act on the seven-pass transmembrane receptors, various substances are known for various receptors. For example, glutamic acid and dopamine (which are both physiological amines) bind to the glutamic acid receptors and the dopamine receptors, respectively. Further, neuropeptide Y and endothelin (which are both peptides) bind to the neuropeptide Y receptors and the endothelin receptors, respectively (Watson, S. and Arkinstall, S., "The G-protein Linked Receptor Facts Book", Academic Press Inc., 1994). Such endogenous substances include both substances (such as chemokines and PAF) which are known to act on the leukocytes, and substances which do not act on the leukocytes.

A substance which activates the seven-pass transmembrane receptor, irrespective of whether natural or artificial, causes various changes in the intracellular signals, and the changes caused in the intracellular signals depend on the states of the substance, the seven-pass transmembrane receptor itself and the cell expressing the receptor. Examples of such changes in the intracellular signals include an increase and decrease in the intracellular CAMP concentration, an increase in the inositol phosphate concentration, and an increase in the intracellular calcium concentration (Watson, S. and Arkinstall, S., "The G-protein Linked Receptor Facts Book", Academic Press Inc., 1994). Methods for measuring each of these changes have been developed. Therefore, by measuring the changes exemplified above, it becomes possible to determine whether a particular substance activates a particular seven-pass transmembrane receptor or inhibits the activation of a particular seven-pass transmembrane receptor. Further, methods for observing physiological phenomena (such as cell proliferation, changes in gene expression, and chemotaxis) which are caused by the binding of the substance to the seven-pass transmembrane receptor are also known in the art, and these phenomena can be used as the indices for determining whether a particular substance activates the seven-pass transmembrane receptor or inhibits the activation of the receptor. As apparent from the above, there are a wide variety of methods for identifying a substance which acts on the seven-pass transmembrane receptor. However, it should be noted that for using such methods for obtaining substances useful as pharmaceuticals for humans, it is first required to obtain a human seven-pass transmembrane receptor protein.

Likewise, if there can be obtained substances which individually act specifically on different types of seven-pass transmembrane receptors (for example, the chemokine receptors), such substances may possibly lead to development of novel pharmaceuticals which each selectively suppress a specific inflammatory reaction and the like.

An explanation is made below taking chemokines as an example. The chemokines and the chemokine receptors regulate the chemotaxis of each of various different leukocytes. Therefore, it is considered that a particular leukocyte expresses a particular chemokine receptor. Actually, there are reports that CCR5 is expressed by Th1 cells and CCR4 is expressed by Th2 cells (Loetscher, P. et al., NATURE, 391, 344–345, 1998; and Bonecchi, R. et al., J. Exp. Med., 187, 129–134, 1998), and the chemokine receptors are considered to participate in the selection of specific cellular and humoral immune responses following an antigen non-specific inflammation. In addition, chemokines, such as CXC and CC chemokines, which act mainly on neutrophils and monocytes are called "Inflammatory chemokines" because these chemokines play an important role in acute or chronic inflammatory reactions. The detection of inflammatory diseases, the diagnosis of the severity of the diseases and the evaluation of the progress of treatment become possible by conducting studies on the receptors for the inflammatory chemokines, for example, by conducting the analysis of the expression of the chemokine receptors in the peripheral blood.

It is considered that the analysis of the receptors will possibly lead to the development of novel methods for the diagnosis and treatment of inflammatory diseases and the like of which the pathogenesis is not known. For example, rheumatism is a cryptogenic, systemic inflammatory disease exhibiting recurrent erosive arthritis as a major symptom thereof while giving impairment to multiple organs. Rheumatism progresses chronically while repeating remission and exacerbation m and leads to the destruction and deformation of joints, and finally causes the functional disorder of motorium. At present, the important factor of the treatment of rheumatism is to diagnose rheumatism at a stage as early as possible and suppress the rheumatic inflammations as soon as possible and as much as possible so as to prevent the occurrence of symptoms, such as joint damages, which are impossible to cure.

As apparent form the above, it is very important to start the treatment of rheumatism at an early stage. During the treatment of rheumatoid arthritis (RA) by the conventional pyramid method (Smyth, C. J., Postgrad. Med., 51, No. 6, 31–39, 1972), the treatment using only a nonsteroidal anti-inflammatory drug (NSAID) is conducted for 3 to 6 months and, then, only after determining that the patient is actually suffering from rheumatoid arthritis (RA), a disease-modifying anti-rheumatic drug (DMARD) is administered to the patient. When RA progresses during the treatment with NSAID, resulting in an increase in the number of arthritic joints, the effect of the DMARD decreases markedly and the prevention of bone damages becomes difficult. Therefore, early diagnosis of RA is necessary for the administration of DMARD to be started at an early stage before the occurrence of bone damages. According to the current criteria for the diagnosis of RA (Arnett, F. C. et al., The American Rheumatism Association 1987 revised criteria for the classification of rheumatoid arthritis, Arthritis Rheum. 31, 315–324, 1988), it is difficult to diagnose RA at the early stage, and at least 6 weeks are necessary for the diagnosis. In the clinical observations, the early RA patients exhibit significantly high values with respect to the sedimentation rate of erythrocytes (wherein erythrocyte sedimentation is a non-specific reaction which is promoted by the destruction and inflammation of tissues) and the amount of CRP (C-reactive protein) which is an acute reaction product which rapidly increases upon the occurrence of the destruction and inflammation of tissues. However, none of these reactions are RA specific, so that they cannot be used for distinguishing RA from other diseases, such as collagenosis. In addition, there are cases of early RA wherein the erythrocyte sedimentation rate is normal, but bone damages are observed by X-ray examination. Further, 71% of the early RA patients who are within 1 year from the onset of RA are positive with respect to the rheumatoid factor, but the rheumatoid factor positive ratio among the RA patients who are within 6 weeks from the onset of RA is only 59%. No significant differences in the numbers of leukocytes and erythrocytes and hemoglobin level are observed between early RA patients (within 1 year from the onset) and early non-RA arthritis patients (Kuniomi YAMAMAE, "Igaku no ayumi (Progress in Medicine)", 182, No. 9, 605–610, 1997).

Thus, although early diagnosis is necessary for the treatment of rheumatism, no diagnostic marker which is useful for the diagnosis of rheumatism has yet been established in the art. Therefore, the early diagnosis of rheumatism is difficult.

SUMMARY OF THE INVENTION

The present inventors have made extensive and intensive studies with a view toward solving the above-mentioned problems. In the course of the studies, the present inventors conceived that immature dendritic cells have a novel seven-pass transmembrane receptor and such a novel receptor is useful for searching pharmaceuticals which can regulate the functions of dendritic cells. First, by employing various methods, such as differential display method (for example, see Liang, P. et al., Curr. Biol., 7, 274–280, 1995), RDA method (Lisitsyn, N. et al., Science, 259, 946–951, 1993) and degenerative PCR method (Innis, M. A. et al., PCR Protocols, 39–53, 1990), the present inventors worked for obtaining a cDNA for a novel seven-pass transmembrane receptor protein expressed in the immature dendritic cells. In particular, with respect to the degenerative PCR method, more than 20 types of primers including those primers used in Example 1 described below were tested. As a result of such extensive and intensive studies, the present inventors successfully obtained a cDNA fragment of a novel seven-pass transmembrane receptor from dendritic cells, and subsequently succeeded in cloning the entire coding region of the obtained cDNA fragment. The present inventors designated the novel seven-pass transmembrane receptor as "C5L2". Further, the present inventors prepared an expression system for the receptor protein encoded by the novel DNA. In addition, the expression of C5L2 in human tissues, leukocytes, leukemia cell lines and the like was examined by northern blotting and it was found that leukocytes, especially granulocytes, exhibit strong expression of C5L2 gene.

Since the structure of the novel seven-pass transmembrane receptor C5L2 protein is similar to those of receptors for chemotactic factors, such as chemokines, FMLP and C5a, studies were made on the possible use of the novel receptor in various fields, such as pharmaceuticals for various inflammatory diseases, and the diagnosis and treatment of various inflammatory diseases. Further, the present inventors considered that the receptor of the present invention should be useful for the diagnosis of inflammatory diseases, and hence made research into the relationship between rheumatism and the receptor C5L2. As a result, it was found that the seven-pass transmembrane receptor C5L2 is useful for the diagnosis of inflammatory diseases. The present invention has been completed, based on these novel findings.

Therefore, it is a primary object of the present invention to provide a human seven-pass transmembrane receptor protein which is advantageous for searching pharmaceuticals which can regulate the functions of dendritic cells.

It is another object of the present invention to provide a DNA encoding the above-mentioned seven-pass transmembrane receptor protein, a recombinant DNA obtained by operably inserting the DNA into an expression vector, and a cell of a microorganism or cell culture, transformed with this recombinant DNA.

Still another object of the present invention is to provide a method for screening a ligand which binds to the seven-pass transmembrane receptor protein, and a method for screening a substance which inhibits the ligand from binding to the seven-pass transmembrane receptor protein.

A further object of the present invention is to provide an antibody which binds to the seven-pass transmembrane receptor protein.

Still a further object of the present invention is to provide a method for the diagnosis of an inflammatory disease, which comprises determining the amount of the seven-pass transmembrane receptor protein expressed in human leukocytes.

The foregoing and other objects, features and advantages of the present invention will be apparent to those skilled in the art from the following detailed description and the appended claims taken in connection with the accompanying drawings and sequence listing.

SEQUENCE LISTING FREE TEXT

In SEQ ID NO:5, the 18th, 22nd and 24th nucleotides "n" represent inosine (i). This sequence is of a degenerative PCR primer designed based on the nucleotide sequences of conventional seven-pass transmembrane receptor proteins which are considered to participate in the proliferation of melanoma.

In SEQ ID NO:6, the 22nd and 28th nucleotides "n" represent inosine (i), and the 21st nucleotide "n" represents a, g, c or t. This sequence is of a degenerative PCR primer designed based on the nucleotide sequences of conventional seven-pass transmembrane receptor proteins which are considered to participate in the proliferation of melanoma.

SEQ ID NO:7 is of a synthetic primer used for constructing the-recombinant DNA containing C5L2 gene, wherein the primer has a sequence obtained by adding the spacer sequence "gggg" and restriction enzyme HindIII recognition site "aagctt" to the 5'-end of a 22-nucleotide sequence corresponding to the 1st (a) to 22nd (t) nucleotides of SEQ ID NO:1.

SEQ ID NO:8 is of a synthetic primer used for constructing the recombinant DNA containing C5L2 gene, wherein the primer has a sequence obtained by adding the spacer sequence "ggga" and restriction enzyme SacII recognition site "ccgcgg" to the 5'-end of a 20-nucleotide sequence corresponding to the 206th (c) to 225th (a) nucleotides of SEQ ID NO:4.

SEQ ID NO:9 is of a synthetic primer used in RT-PCR performed for amplifying C5L2 gene.

SEQ ID NO:10 is of a synthetic primer used in RT-PCR performed for amplifying C5L2 gene.

SEQ ID NO:11 is of a synthetic primer used in RT-PCR performed for amplifying G3PDH gene (glyceraldehyde 3-phosphate dehydrogenase).

SEQ ID NO:12 is of a synthetic primer used in RT-PCR performed for amplifying G3PDH gene (glyceraldehyde 3-phosphate dehydrogenase).

DETAILED DESCRIPTION OF THE INVENTION

Figure 1:
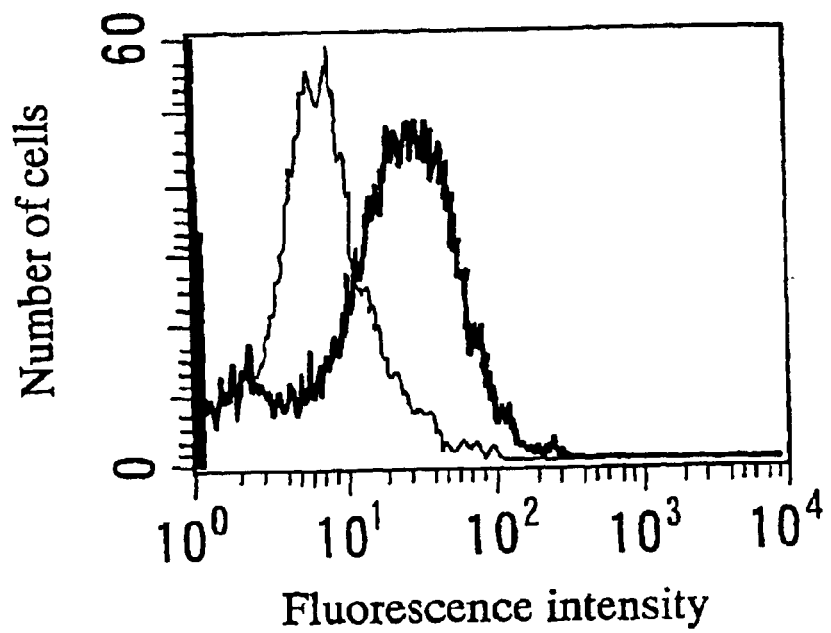
FIGS. 1(a) and 1(b) are histograms obtained by means of a flow cytometer, which respectively show the expression of C5L2 gene on the cell surface of immature dendritic cells and that on the cell surface of mature dendritic cells, wherein the ordinate shows the number of cells and the abscissa shows the amount of antigen present on the cell surface, the amount of antigen being a value expressed in terms of the fluorescence intensity of FITC (fluorescein isothiocyanate)-labeled antibody which has bound to the antigen, and wherein the thick line shows the results of the flow cytometry using biotinylated anti-C5L2 antiserum for the primary labeling, and the thin line shows the results of the negative control using biotinylated anti-rabbit IgG antibody for the primary labeling.
Figure 1:
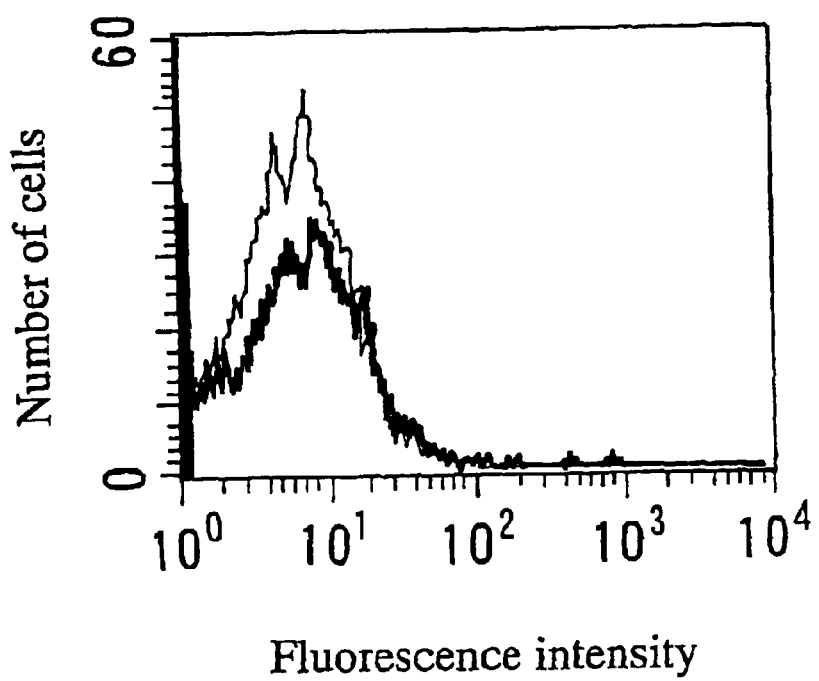

In one aspect of the present invention, there is provided a substantially pure human seven-pass transmembrane receptor protein having the amino acid sequence of SEQ ID NO:2.

For easy understanding of the present invention, the essential features and various preferred embodiments of the present invention are enumerated below.

1. A substantially pure human seven-pass transmembrane receptor protein having the amino acid sequence of SEQ ID NO:2.

2. A purified peptide which is a fragmentary sequence selected from the group consisting of the 6th to 32nd amino acid residues of SEQ ID NO:2, the 1st to 23rd amino acid residues of SEQ ID NO:2, the 1st to 35th amino acid residues of SEQ ID NO:2, the 96th to 108th amino acid residues of SEQ ID NO:2, the 172nd to 198th amino acid residues of SEQ ID NO:2, and the 681st to 726th amino acid residues of SEQ ID NO:2.

3. An isolated DNA encoding the seven-pass transmembrane receptor protein of item 1 above.

4. The isolated DNA according to item 3 above, having the nucleotide sequence of SEQ ID NO:1.

5. An isolated DNA or a chemically modified nucleic acid derivative thereof, wherein the isolated DNA is a fragmentary sequence of at least 20 contiguous nucleotides in the nucleotide sequence of SEQ ID NO:3;

6. An isolated DNA or a chemically modified nucleic acid derivative thereof, wherein the isolated DNA is a fragmentary sequence of at least 20 contiguous nucleotides in the nucleotide sequence of SEQ ID NO:4;

7. An isolated RNA or a chemically modified nucleic acid derivative thereof, wherein the isolated RNA is a fragmentary sequence of at least 20 contiguous nucleotides in an RNA which is complementary to the nucleotide sequence of SEQ ID NO:3.

8. A replicable recombinant DNA, comprising a replicable expression vector and, operably inserted therein, the isolated DNA according to any one of items 3 to 6 above.

9. A cell of a microorganism or cell culture, transformed with the replicable recombinant DNA of item 8 above.

10. A seven-pass transmembrane receptor protein obtainable by a process which comprises:
    (a) ligating, to a replicable expression vector, the isolated DNA according to item 3 or 4 above, to thereby obtain a replicable recombinant DNA having the replicable expression vector and, operably inserted therein, the DNA;
    (b) transforming cells of a microorganism or cell culture with the replicable recombinant DNA to form transformants;
    (c) selecting the transformants from parent cells of the microorganism or cell culture; and
    (d) culturing the transformants, causing the transformants to express the DNA and produce a protein on the cell surface of the transformants.

11. A method for screening a ligand which binds to the seven-pass transmembrane receptor protein of item 1 above, which comprises:
    contacting a protein of item 1 or 10 above, or a peptide of item 2 above, with a sample which is suspected to contain a ligand which binds to the protein or the peptide;
    assessing a change occurring in response to a binding of the ligand to the protein or the peptide; and
    detecting the ligand by using the change as an index.

12. A method for screening a substance which inhibits a ligand from binding to the seven-pass transmembrane receptor protein of item 1 above, which comprises:
    contacting the protein of item 1 or 10 above, or the peptide of item 2 above, with a ligand which binds to the protein or the peptide and a sample which is suspected to contain a substance which inhibits the ligand from binding to the protein or the peptide;
    assessing a change occurring in response to a binding of the ligand to the protein or the peptide; and
    detecting the substance by using the change as an index.

13. An antibody which specifically binds to the seven-pass transmembrane receptor protein of item 1 above.

14. A method for the diagnosis of an inflammatory disease, which comprises determining the amount of a seven-pass transmembrane receptor protein expressed in human leukocytes, wherein the seven-pass transmembrane receptor protein is the protein having the amino acid sequence of SEQ ID NO:2.

15. The method according to item 14 above, wherein the inflammatory disease is rheumatoid arthritis.

16. The method according to item 14 or 15 above, in wherein the human leukocytes are human granulocytes.

17. The method according to item 16 above, wherein the human granulocytes are sampled from human tissue.

18. The method according to item 17 above, wherein the human granulocytes are granulocytes which have been sampled at least six hours before diagnosis.

19. The method according to item 14 above, wherein the amount of the expressed protein is determined by measuring the amount of mRNA encoding the protein.

20. The method according to item 19 above, wherein the amount of the mRNA is measured by RT-PCR method.

21. The method according to item 14 above, wherein the amount of the expressed protein is determined by measuring the amount of the protein present on the cell surface of the leukocytes.

22. The method according to item 21 above, wherein the amount of the protein is measured using an antibody which specifically binds to the protein.

Hereinbelow, the present invention is described in detail.

In the sequence listing, the left end and the right end of the amino acid sequence are the amino terminus (N-terminus) and the carboxyl terminus (C-terminus), respectively, and the left end and the right end of the nucleotide sequence are the 5'-end and the 3'-end, respectively.

In the present invention, with respect to the nucleotide sequences, a represents adenine, c represents cytosine, g represents guanine and t represents thymine.

In the present invention, with respect to the amino acid sequences shown in 3-letter abbreviation, Ala represents an alanine residue, Arg represents an arginine residue, Asn represents an asparagine residue, Asp represents an aspartic acid residue, Cys represents a cysteine residue, Gln represents a glutamine residue, Glu represents a glutamic acid residue, Gly represents a glycine residue, His represents a histidine residue, Ile represents an isoleucine residue, Leu represents a leucine residue, Lys represents a lysine residue, Met represents a methionine residue, Phe represents a phenylalanine residue, Pro represents a proline residue, Ser represents a serine residue, Thr represents a threonine residue, Trp represents a tryptophan residue, Tyr represents a tyrosine residue and Val represents a valine residue.

The term "dendritic cell" used in the present invention means a star-shaped cell having outwardly extending dendrites wherein the star-shaped cell is found in lymph nodes and germinal centers. A dendritic cell is one of the antigen presenting cells derived from hematopoietic stem cells. In recent years, in vitro large scale culture of the dendritic cells became possible (Romani et al., J. Exp. Med., 180, 83–93, 1994). Either undifferentiated CD34 positive cells (obtained from bone marrow or umbilical cord blood) or peripheral blood monocytes can be differentiated into dendritic cells. Specifically, immature dendritic cells can be obtained by stimulating the undifferentiated CD34 positive cells or peripheral blood monocytes with a combination of GM-CSF (Granulocyte Macrophage Colony-Stimulating Factor) and IL-4 (Interleukin 4), and mature dendritic cells can be obtained by stimulating the undifferentiated CD34 positive cells or peripheral blood monocytes with a combination of GM-CSF, IL-4 and TNF-α (Tumor Necrosis Factor-α) (Talmor, M et al., Eur. J. Immunol., 28, 811–817, 1998; and Morse, M A et al., Ann Surg., 226, 6–16, 1997).

In the present invention, the term "leukocyte" is used as a general term covering mononuclear cells (i.e., lymphocytes and monocytes) and granulocytes (i.e., neutrophils, eosinophils and basophils). A granulocyte is a segmented leukocyte having a rod-shaped nucleus or a constricted nucleus. As mentioned above, the group of granulocytes is comprised of neutrophils, eosinophils and basophils.

In the present invention, examples of "human tissue" include body fluids (such as blood, synovial fluid and lymph), tissues and organs (such as lymph nodes, spleen, bone marrow, gastrointestinal tract and synovial membranes). In the present invention, the term "sampling of a tissue" means "taking out a tissue from a body". For example, when the tissue is blood, "sampling of a tissue" means "collection of blood".

The term "inflammation" used in the present invention covers any inflammatory response of the living body, which involves a reaction of the non-specific defense mechanism or a reaction of the specific defense mechanism. The inflammation involving the non-specific defense mechanism is an inflammatory response mediated by leukocytes (including macrophages, eosinophils and neutrophils) which are generally considered to be incapable of immunological memory. Examples of inflammations involving the non-specific defense mechanism include a swelling which occurs immediately after being stung by a bee, and gathering of leukocytes to a site of a bacterial infection (for example, infiltration of leukocytes into the lung suffering from bacterial pneumonia, and the formation of pus in an abscess). The inflammation involving the specific defense mechanism is an immune response which is specific against an antigen. Examples of inflammations involving the specific defense mechanism include a response of antibodies against an antigen (such as virus) and delayed type hypersensitivity.

The term "inflammatory disease" used in the present invention means a disorder in a human body which is caused by hyperfunction or hypofunction of the above-mentioned non-specific and specific defense mechanisms. Therefore, in the present invention, infectious diseases and autoimmune diseases are included in the inflammatory diseases. Usually, an infectious disease is a disease which arises when a malfunction of the immune system (a self-defense system for protecting the living body (host) from infections by exogenous pathogens, such as viruses, bacteria, parasites and fungi) occurs, so that the exogenous pathogens cannot be excluded from the living body. On the other hand, an autoimmune disease is a disease in which the immune system malfunctions to attack the "self" (which should not be attacked but should be defended by the immune system). Two types of autoimmune diseases, namely the autoimmune diseases specific to an organ or tissue and the non-specific systemic autoimmune diseases, are known in the art. A wide variety of autoimmune diseases are known to result from immunomodulation disorders, and examples of such autoimmune diseases include systemic lupus erythematosus, rheumatoid arthritis, type I diabetes, inflammatory bowel disease, biliary cirrhosis, uveitis, multiple sclerosis, Crohn's disease, ulcerative colitis, bullous pemphigoid, sarcoidosis, psoriasis, ichthyosis and Graves' orbitopathy.

A "seven-pass transmembrane receptor protein" mentioned in the present invention is one type of a receptor belonging to the leukocyte receptor family, and this receptor is also called a "G-protein coupled receptor (GPCR)" or a "rhodopsin-type receptor".

With respect to the molecular-biology techniques which are necessary for conducting the operations of gene manipulation described herein (wherein examples of such operations include preparation of cDNAs, determination of gene expression by northern blotting, screening by hybridization, preparation of recombinant DNAs, determination of the nucleotide sequence of a DNA, and preparation of a cDNA library), these techniques are described in reference books. Particularly, reference can be made to, for example, "Molecular Cloning, A laboratory manual", Sambrook, J., Fritsch, E. F. and Maniatis, T. Eds., Cold Spring Harbor Laboratory Press, 1989.

For further illustrating the essential features of the present invention, the technical features included in the present invention will be described below in detail while explaining how the present invention has been developed.

As explained below in detail, a cDNA fragment which encodes the seven-pass transmembrane receptor C5L2 protein of the present invention was obtained from immature dendritic cells, and the whole length cDNA sequence encoding C5L2 protein was obtained from a placental cDNA library. The mRNA of C5L2 was also detected in peripheral leukocytes. The whole length cDNA sequence encoding the seven-pass transmembrane receptor C5L2 protein of the present invention is shown in SEQ ID NO:1 of the sequence listing attached hereto. The nucleotide sequence of SEQ ID NO:1 was compared with the cDNA sequences of various known genes so as to determine the sequence homologies to the known genes. Specifically, by using the computer software GENETYX-Mac/DB Ver. 39.1 (Software Development Co., Ltd., Japan), a homology search was conducted in the database GenBank (Release 106.0, April, 1998) in order to detect registered nucleotide sequences which are homologous to the nucleotide sequence of SEQ ID NO:1. As a result, the below-mentioned ten sequences having the ten top positions in the homology ranking were obtained (in the following list, the entry names are shown in the square brackets, and the percent values indicate the homologies):

P. pygmaeus DNA for C5a receptor [PPC5AR] 56.3%;

G. gorilla DNA for C5a receptor [GGC5AR] 56.7%;

H. sapiens C5aR rRNA for C5 anaphylatoxin receptor [HSC5AR] 56.8%;

Human C5a anaphylatoxin receptor mRNA [HUMC5AAR] 56.8%;

H. sapiens RNA for receptor for C5a anaphylatoxin [HSC5ANAPL] 56.8%;

M. mullata DNA for C5a receptor fragment [MMC5AR] 56.2%;

P. troglodytes DNA for C5a receptor (PTC5AR] 56.6%;

C. familiaris mRNA for complement C5a receptor [CFCOMC5AM] 59.1%;

Rattus norvegicus mRNA for C5a receptor [AB003042] 57.2%; and

R. norvegicus mRNA for C5a receptor [RNC5AREC] 57.2%.

As apparent from the above, the cDNA encoding the seven-pass transmembrane receptor C5L2 protein of the present invention exhibits a homology to the anaphylatoxin receptors C5a-R (Kroll, B. et al., FEBS Lett., 291, 208–210, 1991) of various organisms including humans; however, the homology is only about 56 to 59%.

An amino acid sequence deduced from the nucleotide sequence of the present invention is shown in SEQ ID NO:2.

The amino acid sequence of SEQ ID NO:2 was compared with the amino acid sequences encoded by various known genes so as to determine the sequence homologies to the amino acid sequences encoded by the various known genes. Specifically, by using the computer software GENETYX-Mac/DB Ver. 39.1 (Software Development Co., Ltd., Japan), a homology search was conducted in the database Swiss-Prot (Release 35.0, November, 1997) in order to detect registered amino acid sequences which are homologous to the amino acid sequence of SEQ ID NO:2. As a result, the below-mentioned ten sequences having the ten top positions in the homology ranking were obtained (in the following list, the entry names are shown in the square brackets, and the percent values indicate the homologies):

C5A ANAPHYLATOXIN CHEMOTACTIC RECEPTOR (C5A-R) (CD88) [C5AR-HUMAN] 38.2%;
C5A ANAPHYLATOXIN CHEMOTACTIC RECEPTOR (C5A-R) [C5AR-CANFA] 39.6%;
C5A ANAPHYLATOXIN CHEMOTACTIC RECEPTOR (C5A-R) [C5AR-MOUSE] 38.1%;
FMLP-RELATED RECEPTOR II (FMLP-R-II) (RFP) (HM63) [FML2-HUMAN] 29.9%;
FMET-LEU-PHE RECEPTOR (FMLP RECEPTOR) (N-FORMYL PEPTIDE RECEPTOR) [FMLR-HUMAN] 28.8%;
PROBABLE G PROTEIN-COUPLED RECEPTOR GPR1 [GPR1-RAT] 28.1%;
FMET-LEU-PHE RECEPTOR (FMLP RECEPTOR) (N-FORMYL PEPTIDE RECEPTOR) [FMLR-RABBIT] 29.8%;
FMET-LEU-PHE RECEPTOR (FMLP RECEPTOR) (N-FORMYL PEPTIDE RECEPTOR) [FMLR-MOUSE] 28.5%;
PROBABLE G PROTEIN-COUPLED RECEPTOR GPR1 [GPR1-HUMAN] 28.1%; and
FMLP-RELATED RECEPTOR I (FMLP-R-I) [FML1-HUMAN] 26.3%.

As apparent from the above, the amino acid sequence of the seven-pass transmembrane receptor C5L2 protein of the present invention exhibits a homology to the known seven-pass transmembrane receptors of humans and other mammals; however, the homology is only about 30 to 40%.

From the homology searches described above, it has m been found that the C5L2 receptor found out by the present inventors is a novel one which exhibits an amino acid sequence homology as low as less than 40% to the conventional human and non-human mammalian seven-pass transmembrane receptor proteins. The cDNA sequence encoding C5L2 protein has also been found to be a novel one which exhibits a homology as low as less than 60% to the cDNA sequences encoding the conventional human and non-human mammalian seven-pass transmembrane receptors.

Further, the present inventors analyzed the hydrophobic regions and the hydrophilic regions of the amino acid sequence of SEQ ID NO:2 in accordance with the method of Kyte-Doolittle (J. Mol. Biol., 157, 105–132, 1982). The results of this analysis indicate that C5L2 is expressed on the cell surface as a cell membrane protein having seven transmembrane regions. In addition, with respect to the results of the homology searches described above, the results show that all of the above-mentioned known sequences which were found to have a homology to the C5L2 protein are seven-pass transmembrane receptor proteins. Based on these facts, it is concluded that the protein of the present invention is a novel seven-pass transmembrane receptor protein.

It is known in the art that, with respect to the conventional receptor proteins, the homology among the species is high. For example, in the case of angiotensin receptor Ia, the homology between human Ia (Swiss-Prot Entry: AG2R-Human) and rat Ia (Swiss-Prot Entry: AC22-Rat) is more than 90%. However, in the case of the seven-pass transmembrane receptor C5L2 of the present invention, no highly homologous sequences were found in the database. Therefore, it is considered that C5L2 is not a human counterpart of any receptor already known in other species, but is a novel receptor.

C5L2 protein of the present invention has a homology (although not high) to anaphylatoxin receptor C5a-R and, hence, C5L2 is considered to belong to the same subfamily as that of the human anaphylatoxin receptors. According to recent reports, human anaphylatoxin receptor C5a-R (Kroll, B. et al., FEBS Lett., 291, 208–210, 1991), human anaphylatoxin receptor C3a-R (Crass, T. et al., Eur. J. Immunol., 26, 1944–1950, 1996), bacterial peptide FMLP receptor (Boulay, F. et al., Biochem. Biophys. Res. Commun., 168, 1103–1109, 1990), ChemR23 (Samson, M. et al., Eur. J. Immunol., 28, 1689–1700, 1998) and the like belong to a single subfamily within the GPCR family, as judged from the homology among the above-mentioned receptors (Samson, M. et al., Eur. J. Immunol., 28, 1689–1700, 1998). It is known that all of the receptors belonging to this subfamily greatly participate in immunoregulation (for example, anaphylatoxin receptors C3a-R and C5a-R participate in allergy and inflammatory reactions; FMLP-R's participate in the defense against infections; and ChemR23 participates in the induction of immunity mediated by an antigen presenting cell, such as a dendritic cell or a macrophage). In view of the fact that C5L2 receptor of the present invention belongs to the above-mentioned subfamily, the present inventors presumed that C5L2 also greatly participates in the immunoregulation in inflammations and infections, and the present inventors made further studies on the relationship between C5L2 and inflammatory diseases. In the further studies, northern blotting analyses showed that the peripheral leukocytes, especially granulocytes, exhibit strong expression of C5L2 gene.

Further, the present inventors considered that it is possible that the ratio of the C5L2 gene expression in sampled body fluids or tissues changes with time during the storage. In order to examine such a possible change in ratio of C5L2 gene expression, the present inventors fractionated granulocytes from peripheral blood both immediately after collection thereof and after storage thereof for a predetermined period of time, and they analyzed how the ratio of the expression of C5L2 gene in granulocytes changes with time during the storage. As a result, it was found that, in the granulocytes obtained from the peripheral blood of healthy donors, the amount of mRNA encoding C5L2 protein decreased with time during the storage of the collected blood. Specifically, in the granulocytes obtained from healthy persons, the amount of the mRNA decreased rapidly during the period of time of 0 to 6 hours after the collection of the blood, and then decreased gradually, wherein the decrease in amount of the mRNA continued for 24 hours after the collection of the blood. On the other hand, it was also found that, in the granulocytes obtained from the peripheral blood of RA patients, the amount of the mRNA encoding C5L2 did not decrease even when stored for 24 hours after the collection of the blood. Such a phenomenon is not observed in the case of the chemokine receptors CCR4 and CCR5 and, thus, the present inventors have found that this phenomenon is specific to C5L2.

As a result of the above-mentioned extensive and intensive studies, the present inventors have found that the change in ratio of the expression of C5L2 gene in collected blood is useful as a marker for inflammatory diseases. The present invention has been completed, based on these novel findings.

According to the present invention, there are provided not only a whole length protein of the seven-pass transmembrane receptor C5L2 protein but also fragmentary peptides thereof.

The seven-pass transmembrane receptor C5L2 protein of the present invention is expressed strongly in peripheral leukocytes, especially granulocytes, and it is a novel protein found out for the first time by the present inventors. The protein of the present invention has such characteristics that the protein has the ability to associate with a ligand specific for the receptor C5L2, and the ability to participate in the signal transduction pathway so as to transduce a signal to the downstream of C5L2 in the signal transduction pathway.

One example of such a protein is a protein having the amino acid sequence of SEQ ID NO:2, but the protein of the present invention is not limited to one having this amino acid sequence. With respect to the protein of the present invention, there is no particular limitation as long as the protein is a polypeptide exhibiting, as a receptor protein, the above-mentioned characteristics. Examples of such proteins include naturally occurring variant proteins or polypeptides found within the same species, and modified proteins or polypeptides (i.e., an amino acid sequence obtained by deletion, replacement or addition of 1 or more amino acids) resulting from a spontaneous mutation, such as an allelic mutation. For example, a method for the modification of an amino acid sequence (particularly by the replacement of amino acid residues) is described in detail in the patent application by Bennett et al. (International patent application publication No. WO 96/02645), and the modified proteins can be prepared referring to the disclosure of the above-mentioned publication. Further, examples of the protein of the present invention also include salts of the above-mentioned proteins.

The protein of the present invention may be one which has been subjected to post-translational modifications. The amino acid sequence of SEQ ID NO:2 contains regions which are susceptible to sugar chain addition. For example, the asparagine residue (Asn) at the 3rd position in the amino acid sequence of SEQ ID NO:2 is considered to be the Asn of the sequence Asn-X-Ser/Thr, which is the consensus sequence susceptible to a modification to form an N-glycoside linkage. Thus, the Asn at the 3rd position has the possibility of undergoing N-glycosylation. In addition, a serine- or threonine-rich region of a protein is presumed to be a region which is susceptible to a modification to form an O-glycoside linkage with N-acetyl-D-galactosamine. In general, a glycosylated protein is not only more stable against in vivo decomposition than a non-glycosylated protein, but also exhibits a stronger physiological activity than a non-glycosylated protein. Therefore, the protein of the present invention embraces a protein having a structure wherein the amino acid sequence of SEQ ID NO:2 has sugar chain(s) (such as N-acetyl-D-glucosamine or N-acetyl-D-galactosamine) which is bonded thereto through an N-glycoside or O-glycoside linkage.

In addition, the protein of the present invention may contain conventional tag sequences, such as an antigenic epitope. Examples of tag sequences include FLAG (MDYKDDDDK) (SEQ ID NO: 13), T7 (MASMTGGQQMG) (SEQ ID NO: 14), HSV (SQPELAPEDPED) (SEQ ID NO: 15), S (KETAAAKFERQHMDS) (SEQ ID NO: 16), Myc (EQKLISEEDL) (SEQ ID NO: 17), His (HHHHHHHH) (SEQ ID NO: 18) and HA (YPYDVPDYA)(SEQ ID NO: 19) (the above sequences in parentheses are shown in 1-letter amino acid abbreviation). When the tag sequence is present in the C-terminal region or the N-terminal region of the C5L2 protein, the detection of the protein by flow cytometry or western blotting (immunoblotting) becomes easy.

The C5L2 protein and the fragments thereof are useful for producing an antibody for use in diagnosis and useful for screening pharmaceuticals for treating diseases. Each of the above-mentioned fragments is a fragmentary peptide having a part of the amino acid sequence of C5L2 protein, specifically a peptide which is a fragmentary sequence of at least 5 contiguous amino acids in the whole C5L2 protein. Like the whole protein, such a fragmentary peptide is useful for the production of an antibody, the screening of a ligand, and the detection of a substance which binds to C5L2 on dendritic cells thereby regulating the functions of dendritic cells so as to treat diseases. For example, a peptide having a sequence of 5 to 8 amino acid residues of an extracellular region or an intracellular region of the receptor is suitable as an antigen used in the preparation of an antibody. Specifically, for example, the fragmentary peptides used in Example 9 of the present specification, namely a fragmentary peptide consisting of the 6th to 32nd amino acid residues of the amino acid sequence of SEQ ID NO:2 and a fragmentary peptide consisting of the 1st to 23rd amino acid residues of the amino acid sequence of SEQ ID NO:2, can be used as antigens. As an example of fragmentary peptides used for screening a ligand, there can be mentioned a peptide having a sequence which is considered to be ligand-binding region(s) of C5L2. More specific examples of such fragmentary peptides include a peptide containing the N-terminal extracellular region (the 1st to 35th amino acid residues of SEQ ID NO:2), the 1st extracellular loop (the 96th to 108th amino acid residues of SEQ ID NO:2), the 2nd extracellular loop (the 172nd to 198th amino acid residues of SEQ ID NO:2), or the 3rd extracellular loop (the 681st to 726th amino acid residues of SEQ ID NO:2) of C5L2 protein.

With respect to the methods for obtaining the protein of the present invention and fragmentary peptides thereof, there is no particular limitation. As examples of such methods, there can be mentioned a method in which an artificial peptide is synthesized, based on the information of the amino acid sequence, and a method in which a DNA encoding the peptide is introduced into a host cell, and the host cell is caused to produce the peptide. With respect to the method for producing a peptide by introducing a DNA encoding the peptide into a host cell, there can be employed various methods described in publications, such as reference books (for example, Kriegler, "Gene Transfer and Expression—A Laboratory Manual", Stockton Press, 1990; and YOKOTA et al., "Baio-manuaru shiriizu 4, Idenshi-dounyu-to Hatsugen Kaiseki-hou (Bio-Manual Series 4, Methods for Gene Transfer and Expression, and Analysis Methods therefor)" published in 1994 by YODOSHA CO., LTD., Japan).

According to the present invention, there is also provided a DNA encoding the above-mentioned seven-pass transmembrane receptor C5L2 protein.

An example of the DNA encoding the seven-pass transmembrane receptor C5L2 protein is a human cDNA of the present invention, which has a nucleotide sequence shown in SEQ ID NO:1 together with the amino acid sequence derived therefrom. Further, a DNA sequence obtained from the C5L2 mRNA sequence is shown in SEQ ID NO:3, and a DNA sequence complementary to the DNA sequence of SEQ ID NO:3 is shown in SEQ ID NO:4. The sequence of SEQ ID NO:3 is a nucleotide sequence consisting essentially of the DNA sequence of SEQ ID NO:1 and the non-coding regions which are located at the 5'- and 3'-ends (the 5' non-coding region and 3' non-coding region respectively correspond to the 1st to 71st nucleotides and the 1,086th to 1,287th nucleotides of SEQ ID NO:3). Due to the degeneracy of genetic codes, it is possible that a nucleotide sequence mutates without causing mutations in the amino acid sequence encoded thereby, and such mutation of a nucleotide sequence is frequently observed in a genomic DNA isolated from an organism or a cDNA. The naturally occurring mutants and the nucleotide sequences containing a mutation based on the degeneracy of genetic codes are included in the DNA of the present invention. In addition, it should be noted that mutation is likely to occur in the nucleotide sequences of the 5' and 3' non-coding regions because the sequences of these regions do not participate in the determination of an amino acid sequence of a protein. The DNA of the present invention includes DNA sequences containing such a mutation in the non-coding region(s) as well as the mutant nucleotide sequences containing the above-mentioned mutation based on the degeneracy of genetic codes.

The whole length nucleotide sequence of C5L2 obtained by the present inventors is shown in SEQ ID NO:1. A C5L2 clone having a nucleotide sequence which is different from that of SEQ ID NO:1 has also been identified. As a specific example of such clones, a C5L2 clone has been detected, which has a structure in which a further thymine (t) is inserted to the sequence of six contiguous thymines at the site of the 724th to 729th nucleotides of SEQ ID NO:1 (that is, the C5L2 clone has a sequence of seven contiguous thymines at the site which substantially corresponds to the 724th to 729th nucleotides of SEQ ID NO:1). By the use of a nucleic acid probe or primer containing the above-mentioned site of C5L2 of the present invention (i.e., the site consisting of contiguous thymines), it is possible to detect separately a sequence having six contiguous thymines and a sequence having seven contiguous thymines.

With respect to the method for obtaining a DNA encoding the C5L2 protein of the present invention, the DNA can be synthesized based on the nucleotide sequence of SEQ ID NO:1, 3 or 4. When a natural DNA encoding the C5L2 protein is needed, the DNA can be extracted from tissues which have been confirmed to express C5L2, for example, immature dendritic cells, and leukocytes derived from normal peripheral blood. Alternatively, the natural DNA can also be obtained from a placenta cDNA library as in Example 2 of the present specification. Further, the DNA shown in SEQ ID NO:1 (which encodes the C5L2 protein) can be isolated from a transformant (for example, *E. coli*: DH5-pcDNAC5L2 deposited by the present inventors) obtained by transformation with a recombinant DNA which contains a cDNA encoding the whole length amino acid sequence of the C5L2 protein.

Further, according to the present invention, there are also provided an isolated DNA and a derivative thereof, wherein the isolated DNA is a fragmentary sequence of at least 12 contiguous nucleotides in the nucleotide sequence of SEQ ID NO:3 or 4; and an isolated RNA and a derivative thereof, wherein the isolated RNA is a fragmentary sequence of at least 12 contiguous nucleotides in an RNA which is complementary to the nucleotide sequence of SEQ ID NO:3.

As described above, the gene of the present invention has only a low homology (less than 60%) to other known genes and, therefore, it is difficult to clone the gene of the present invention by cross-hybridization or the like using other known genes as a probe. A number of reports have been made on the cloning of a gene by cross-hybridization (for example, Murphy, P. M. et al., Science, 253, 1280–1283, 1991; and Combadiere, C. et al., J. Biol. Chem., 270, 16491–16494, 1995), but the cloning of the seven-pass transmembrane receptor C5L2 of the present invention has never been reported. As shown in the Examples of the present specification, no clone which is considered to be a known receptor gene is detected by the screening of a cDNA library using a part of the cDNA sequence of C5L2 (see Example 2), and no transcript which is considered to be a known receptor gene has been detected by northern blotting using a part of the cDNA sequence of C5L2 (see Example 3). This clearly shows that it is difficult to clone the gene of the present invention by cross-hybridization using a known gene. The DNA or RNA fragment of the present invention is useful for detecting a cDNA of C5L2 or a fragment thereof, or a genomic C5L2 DNA or a fragment thereof from among other DNAs.

Examples of nucleic acid fragments useful for detecting a C5L2 cDNA or a genomic C5L2 DNA include a fragment comprising a sequence of at least 12 contiguous nucleotides, preferably not less than 16 contiguous nucleotides, more preferably not less than 20 contiguous nucleotides, in the nucleotide sequence of SEQ ID NO:1 or 3, or in a DNA or an RNA which is complementary to the nucleotide sequence of SEQ ID NO:1 or 3. A derivative of the above-mentioned nucleic acid fragments can also be used. The length of the nucleic acid fragment may vary depending on the desired properties of the nucleic acid fragment, such as the specificity and the stability of binding to a nucleic acid to be detected. When PCR (Polymerase Chain Reaction) is conducted using a DNA fragment as a primer, it is preferred to use a DNA fragment having a $T_m$ (melting temperature of DNA duplex) of 45° C. or more. In the PCR and the like where two DNA strands are bound to each other thereby forming a DNA duplex, the $T_m$ of the DNA duplex can be estimated by calculating the sum of the temperature values assigned to GC pairs and AT pairs in the DNA duplex, wherein 4° C. is assigned to each GC pair and 2° C. is assigned to each AT pair. When a nucleotide sequence to be detected has a high GC content (90% or more), a DNA fragment which is a sequence of at least 12 contiguous nucleotides can be used. Generally, the GC content of a nucleotide sequence is about 50%. For detecting such a sequence, a DNA fragment which is a sequence of at least 16 contiguous nucleotides is needed. The binding between a DNA and a nucleic acid derivative is more stable than the binding between two DNAs and, thus, when a nucleic acid derivative is used as a primer, it is possible to detect a desired DNA using a short nucleic acid sequence as compared to the case where a DNA is used as a primer.

The examination of the ratio of the expression of the gene of the present invention for the purpose of diagnosis can be conducted by hybridization, primer extension, nuclease protection assay, reverse transcription PCR (RT-PCR) or the like in which a probe or primer designed based on the present invention is used. The probe and primer can be the DNA of SEQ ID NO:4 (i.e., antisense DNA having the sequence complementary to the DNA of SEQ ID NO:3), an RNA complementary to the DNA of SEQ ID NO:3 (i.e., antisense RNA), or a nucleic acid fragment which is a sequence of at least 12 contiguous nucleotides, preferably not less than 16 contiguous nucleotides, more preferably not less than 20 contiguous nucleotides in the above-mentioned DNA or RNA. The antisense DNA or RNA may be a methylated, methyl phosphorylated, deaminated or thiophosphorylated antisense nucleic acid derivative. For example, as shown in Example 4 described below, it is possible to detect the C5L2 mRNA using a fragment of the nucleotide sequence of SEQ ID NO:4 (i.e., the sequence complementary to the DNA of SEQ ID NO:3).

Further, by using the nucleotide sequence of the present invention, a homologue of the gene of the present invention can be detected and cloned from organisms other than human (for example, rat). By the use of the DNA or RNA, or a fragment thereof of the present invention, it is also possible to clone a genomic gene from organisms including human and mouse. Moreover, it is possible to conduct further studies on the gene of the present invention using genetic engineering techniques which have recently been developed, for example, preparation of transgenic mice, gene targetting mice or double knockout mice (i.e., mice in which the gene of the present invention and a gene related thereto are both disrupted). If a disorder is found in a genomic gene of the present invention, such a disordered gene can be utilized for gene diagnosis or gene therapy.

For the purpose of elucidating the specific functions of the seven-pass transmembrane receptor C5L2 protein of the present invention, an antisense nucleic acid can be administered to cells or a living body. For example, with respect to a disease in which the morbidity is caused by the excess action of the C5L2 protein, the treatment of the disease can be effected by suppressing the expression of C5L2 using an anti-sense nucleic acid. In order to administer an antisense nucleic acid, a recombinant nucleic acid obtained by inserting an antisense nucleic acid into an appropriate vector may be used. With respect to the methods for producing such an antisense nucleic acid and the usages of the antisense nucleic acid, reference can be made to Murray, J. A. H. ed., ANTISENSE RNA AND DNA, Wiley-Liss, Inc., 1992.

According to the present invention, there is also provided a recombinant DNA comprising any one of the above-mentioned DNAs of the present invention.

With respect to the vector used for preparing a recombinant DNA of the present invention, there is no particular limitation, and a conventionally employed vector can be used. Examples of vectors include plasmid vectors derived from E. coli (for example, pBR322, pUC8, pUC18, pUV19 and pUC119, each manufactured and sold by TAKARA SHUZO CO., LTD., Japan), plasmid vectors derived from Bacillus subtilis, and plasmid vectors derived from yeasts, bacteriophage vectors (for example, λgt10 and λgt11, each manufactured and sold by Stratagene Cloning Systems, USA); and animal viruses, such as retroviruses and vaccinia virus. Other vectors can also be used as long as the vector can proliferate in the host cell. A representative example of the recombinant DNA of the present Invention is a recombinant DNA containing pcDNA3.1/Myc-His(+)B as a vector (see Example 4). An international deposit of E. coli DH5 transformed with pcDNAC5L2 containing a cDNA encoding the whole length amino acid sequence of the seven-pass transmembrane receptor C5L2 protein of the present invention, namely, E. coli: DH5-pcDNAC5L2 (deposit number: FERM BP-6833), was made with National Institute of Biosience and Human-Technology, Agency of Industrial Science and Technology (1–3, Higashi 1-chome, Tsukuba-shi, Ibaraki-ken, Japan (Postal code No. 305-0046)) on Sep. 1, 1998 (original deposit date).

It is preferred that the recombinant DNA of the present invention is introduced into a conventional host cell. Therefore, the present invention also provides a cell of a microorganism or cell culture, transformed with the recombinant DNA of the present invention.

With respect to the host cell to be transformed with the recombinant DNA of the present invention, there is no particular limitation as long as the host cell is a cell of a microorganism or a cell culture which can express the recombinant DNA of the present invention. For example, the recombinant DNA of the present invention can be introduced into procaryotlc cells, such as bacteria belonging to genus Escherichia (for example, E. coli) and bacteria belonging to genus Bacillus (for example, Bacillus subtilis), by using the calcium chloride method or the like. Examples of bacteria belonging to genus Escherichia include Escherichia coli strains, such as K12, HB101, MC1061, LE392, JM109 and INVαF'. Examples of bacteria belonging to genus Bacillus include Bacillus subtilis M1114. When a bacteriophage is used as a vector, the recombinant DNA of the present invention can be introduced into proliferating E. coli cells by, for example, in vitro packaging method (Proc. Natl. Acad. Sci., 75, 4242–4246, 1978). Eucaryotic cells, such as animal cells and insect cells, can also be used as a host.

Still further, the present invention provides a seven-pass transmembrane receptor protein produced on the cell surface of transformants. Specifically, there is provided C5L2 protein obtainable by a process which comprises:

(a) ligating, to a replicable expression vector, the DNA encoding C5L2 protein, to thereby obtain a replicable recombinant DNA having the replicable expression vector and, operably inserted therein, the DNA;

(b) transforming cells of a microorganism or cell culture with the replicable recombinant DNA to form transformants;

(c) selecting the transformants from parent cells of the microorganism or cell culture; and (d) culturing the transformants, causing the transformants to express the DNA and produce a protein on the cell surface of the transformants.

The recombinant DNA used for producing C5L2 protein on the cell surface of the transformants may contain an initiation codon and a termination codon which are, respectively, positioned at the 5'-end and the 3'-end of the DNA encoding C5L2 protein, which DNA has been inserted into the vector. The addition of the initiation codon or the termination codon to the DNA can be conducted using an appropriate synthetic adapter sequence. For expressing a desired DNA, it is preferred that a promoter is connected to the upstream of the DNA. With respect to promoters used in the present invention, there is no particular limitation as long as the promoter is compatible with the host used for gene expression. When the host is a bacterium belonging to genus Escherachia, tac promoter, trp promoter, lac promoter and the like are preferred. When the host is a bacterium belonging to genus Bacillus, SPO1 promoter, SPO2 promoter and the like are preferred. When the host is a procaryotic cell, it is preferred that the recombinant DNA to be introduced into the host has a ribosome-binding site as well as a promoter. When the host is a yeast, PGK promoter, GAP promoter, ADH promoter and the like are preferred. When the host is an animal cell, an SV40-derived promoter, a retroviral promoter, metallothionein promoter, a heat shock promoter and the like can be used.

With respect to the DNA used for the production of C5L2 protein of the present invention, there is no particular limitation as long as the DNA encodes C5L2 protein having the amino acid sequence of SEQ ID NO:2. Specifically, the nucleotide sequence of SEQ ID NO:1 can be used for producing C5L2 protein. Further, for producing a modified C5L2 having a specific additional function, a conventional nucleotide sequence may be ligated to a DNA encoding C5L2. For example, for ensuring that C5L2 receptor is expressed on the cell surface, a DNA encoding a signal peptide may be added to the 5'-end of the DNA encoding C5L2 protein (wherein the 5'-end corresponds to the N-terminus of the peptide). Further, for facilitating the detection of the produced protein C5L2, a DNA encoding an antigenic epitope may be added to the DNA encoding C5L2 protein. With respect to examples of such techniques, reference can be made to, for example, Choe, H. et al., Cell, 85, 1135–1148, 1996.

A transformant used for producing C5L2 protein can be obtained by introducing the thus constructed recombinant DNA into a host cell capable of expressing the recombinant DNA. Examples of host cells include the above-mentioned bacteria belonging to genus Escherichia, bacteria belonging to genus Bacillus, yeasts and animal cells. Preferred host cells are animal cells, for example, COS-7 (which is a simian cell), Vero cell (which is a simian cell), CHO (which is a Chinese hamster cell) and SF9 (which is a silkworm cell). As shown in Examples 5 and 7 of the present specification, it is easy to introduce the above-mentioned recombinant DNA into cells of 293 cell line or CHO cells by gene transfer techniques thereby obtaining transformants. By culturing the obtained transformants, the transformants can be caused to express the DNA and produce C5L2 protein on the cell surface of the transformants. The production of C5L2 protein by the cultured transformants can be confirmed by western blotting (as in Example 5 described below) or by means of FACS (fluorescence activated cell sorter).

By using the seven-pass transmembrane receptor protein of the present invention, the screening of a ligand which binds to the seven-pass transmembrane receptor protein can be performed. Specifically, in the present invention, there is provided a method for screening a ligand which binds to the seven-pass transmembrane receptor protein of the present invention, which comprises:

contacting a substantially pure receptor C5L2 protein, a fragmentary peptide having a part of the amino acid sequence of C5L2, or C5L2 produced on the cell surface of transformants, with a sample which is suspected to contain a ligand which binds to the protein or the peptide;

assessing a change occurring in response to a binding of the ligand to the protein or the peptide; and detecting the ligand by using the change as an index.

The C5L2 protein used in the above-mentioned screening method of the present invention may be either in a purified form or in a non-purified form; however, it is required that the C5L2 protein exhibit substantially the same ligand-binding activity as exhibited in vivo. Examples of non-purified C5L2 proteins include cell membrane fractions, and natural cells having C5L2 receptor expressed on the cell surface thereof, and transformants having C5L2 protein expressed on the cell surface thereof.

With respect to the sample used in the above-mentioned screening method of the present invention (i.e., a sample which is suspected to contain a ligand which binds to the protein or the peptide), there is no particular limitation. Examples of such samples include an extract or a culture supernatant of tissues or cells obtained from a living body, wherein the extract or culture supernatant is suspected to contain the ligand; a synthetic compound; and a culture supernatant of a microorganism. In view of the fact that the receptor protein of the present invention has a homology to the conventional human anaphylatoxin receptor, it is possible that the ligand for C5L2 is not a substance belonging to the chemokine family, but is another type of a substance, such as a peptide hormone (e.g., somatostatin, anglotensin or bradykinin), a complement or a microbial component.

With respect to the method for detecting the ligand for C5L2, there is no particular limitation. Examples of such detection methods include a method in which, after contacting C5L2 with the sample, the amount of the resultant complex of C5L2 and any ligand is measured and/or the amount of a remaining non-binding portion of the sample is measured, and a method in which, after contacting C5L2 with the sample, a reaction caused by the binding between the sample and C5L2 is measured. With respect to the measurement of the amount of the complex of C5L2 and a ligand and the measurement of the amount of a remaining non-binding portion of the sample, there can be mentioned a method in which the sample is labeled with a radioactive compound, a dye or the like before being contacted with C5L2, and, after contacting C5L2 with the labeled sample, the resultant C5L2-ligand complex is separated from a remaining non-binding portion of the sample; and the amount of the C5L2-ligand complex and/or the amount of the remaining non-binding portion of the sample is measured using the label. As an example of this measuring method, Example 6 of the present specification uses a method in which the amount of a remaining non-binding portion of a radio-labeled, ligand candidate compound (suspected ligand) is measured using the radioactivity. Alternatively, when a substance which binds to the receptor has already been identified, a binding of a sample to the receptor can be measured by a method in which the above-mentioned substance is labeled, and whether or not the sample competes with the labeled substance in binding to the receptor is examined. Specific examples of these methods are described in, for example, Masato ASANUMA et al., "Jikken Igaku 11 (Experimental Medicine 11)", 22–29, 1993. In addition, there can also be mentioned a method (such as SPA (Scintillation Proximity Assay)) in which a binding of a ligand to the receptor is measured without separating a C5L2-ligand complex from a remaining non-binding portion of the sample.

With respect to the method for measuring a reaction caused by the binding between the sample and C5L2, various methods are conceivable which employ signal transduction pathways in which C5L2 participates. Examples of such methods include a method in which an intracellular calcium concentration is measured (Hideaki KARAKI et al., "Jikken Igaku 7 (Experimental Medicine 7)", 26–109, 1989), and a method in which a microphysiometer is used (Samson, M. et al., Biochem. 35, pp. 3362–3367, 1996), and a method in which the content of intracellular cAMP is measured. As an example of such methods, Example 7 of the present specification employs a method in which whether or not C5L2 transformant cells exhibit chemotaxis in the serum of an LPS-administered rat is observed.

As examples of methods for performing the screening of a ligand by using a fragmentary peptide having a part of the amino acid sequence of the seven-pass transmembrane receptor protein of the present invention, there can be mentioned a method using BIACORE™ and a method which is based on purification using a resin column. BIACORE™ is an apparatus which detects the association of two proteins by utilizing surface plasmon resonance ("Tanpakushitsu, Kakusan, Kouso (Protein, Nucleic Acid and Enzyme)", 37, 2977–2984, 1992). The apparatus BIA- CORE™ is used in the following manner. The purified peptide of the present invention, preferably an N-terminal extracellular region of the peptide, is fixed to the sensor chip of BIACORE™, and a sample which is a ligand candidate (suspected ligand) for the peptide of the present invention is added onto the peptide, and whether or not a binding of the sample to the peptide occurs is examined (i.e., whether or not the sample is a ligand for the peptide of the present invention is examined). With respect to the method which is based on purification using a resin column, this method can be performed in the following manner. First, an affinity column for column chromatography is prepared wherein the column contains a resin having fixed thereto the fragmentary peptide of the present invention. Then, by conducing affinity chromatography using the affinity column, a ligand for human C5L2 protein can be purified from, for example, a supernatant of a cell culture. The purified ligand can be isolated and identified.

The ligand thus obtained by a screening method using the whole protein of the present invention or a fragmentary peptide of the present invention is useful for searching a substance which acts on the seven-pass transmembrane receptor C5L2 protein on dendritic cells thereby regulating the functions of dendritic cells so as to treat diseases.

When a ligand for the seven-pass transmembrane receptor C5L2 protein of the present invention has been found (wherein such a ligand is a substance which acts on C5L2 receptor), it becomes possible to search a substance which can change the activity of the ligand on C5L2 receptor, i.e., a substance which either promotes or inhibits a reaction caused by a binding of the ligand to C5L2 receptor. As an example of methods for searching such a substance, there can be mentioned a method for screening a substance which inhibits a ligand from binding to the seven-pass transmembrane receptor C5L2 protein, which comprises:

contacting a substantially pure receptor C5L2 protein, a fragmentary peptide having a part of the amino acid sequence of C5L2, or C5L2 receptor produced on the cell surface of transformants, with a ligand which binds to the protein or the peptide and a sample which is suspected to contain a substance which inhibits the ligand from binding to the protein or the peptide;

assessing a change occurring in response to a binding of the ligand to the protein or the peptide; and detecting the substance by using the change as an index.

As an example of specific methods for performing the screening of a substance which inhibits a ligand from binding to C5L2 receptor, there can be mentioned a method in which whether or not C5L2 transformant cells exhibit chemotaxis is observed, i.e., the method employed in Example 8 described below.

Like a ligand for C5L2 receptor, a substance which inhibits a ligand from binding to C5L2 receptor is also useful. That is, a substance which inhibits a ligand from binding to the protein or peptide of the present invention is useful as a substance which acts on the seven-pass transmembrane receptor protein C5L2 on dendritic cells thereby regulating the functions of dendritic cells so as to treat diseases.

As examples of methods in which a fragmentary peptide having a part of the amino acid sequence of the seven-pass transmembrane receptor C5L2 protein of the present invention is used for the screening of a substance which inhibits a ligand from binding to C5L2 receptor, there can be mentioned the same methods as used for screening a ligand for C5L2 receptor, i.e., a method using BIACORE™ and the like.

Further, in the present invention, there is provided an antibody specifically recognizing the seven-pass transmembrane receptor protein of the present invention.

With respect to the antigen used for producing the antibody of the present invention, there is no particular limitation as long as the antigen has an amino acid sequence of a sufficient length for exhibiting the characteristics of the C5L2 protein. It is preferred that the antigen is a peptide which is a fragmentary sequence of at least 5 contiguous amino acids in the amino acid sequence of SEQ ID NO:2, more advantageously at least 8 contiguous amino acids in the amino acid sequence of SEQ ID NO:2. The antigen peptide is used as such or after cross-linking the peptide with a carrier protein, such as KLH (Keyhole Limpet Hemocyanin) or BSA (bovine serum albumin). The antigen peptide (as such or in a form cross-linked with a carrier protein) is inoculated into an animal, wherein, if desired, an adjuvant may be administered together with the antigen peptide. Subsequently, from the animal, an antiserum containing an antibody (polyclonal antibody) recognizing the C5L2 protein can be obtained. The antiserum can be used as such. If desired, the antibody may be purified from the antiserum. Examples of animals into which the antigen peptide is inoculated include a sheep, a cattle, a goat, a rabbit, a mouse, a rat and the like. For the preparation of a polyclonal antibody, the use of a sheep or a cattle is preferred. Specifically, as shown in Example 9 described below, there can be obtained an anti-human C5L2 protein rabbit polyclonal antibody and a solution of an anti-human C5L2 protein rabbit immunoglobulin.

Further, a monoclonal antibody can be obtained by a conventional method for producing a hybridoma cell. For the production of a monoclonal antibody, it is preferred to use a mouse. As an antigen peptide, there may be used a fusion protein which is obtained by linking GST (glutathione S-transferase) to an antigen peptide which is a fragmentary sequence of at least 5 contiguous amino acids in the amino acid sequence of SEQ ID NO:2, preferably at least 8 contiguous amino acids in the amino acid sequence of SEQ ID NO:2. The fusion protein may be either a purified one or a non-purified one. Also, a monoclonal antibody can be obtained by using a gene recombinant antibody which has been expressed in a cell by using an immunoglobulin gene which has been separated by using various methods described in a reference book ("Antibodies a laboratory manual", E. Harlow et al., Cold Spring Harbor Laboratory) and using a gene cloning method.

The antibody of the present invention can be used for purifying the seven-pass transmembrane receptor C5L2 protein. Further, the antibody which specifically recognizes the seven-pass transmembrane receptor C5L2 protein can be used for the detection and quantitative determination of C5L2, and, hence, the antibody can be used as a diagnostic reagent for the diagnosis of diseases involving abnormal differentiation of cells and autoimmune diseases, such as malignant tumors, viral infections and rheumatism. The detection and quantitative determination of C5L2 by using the antibody can be performed by western blotting, FACS or the like. With respect to the details of western blotting, reference can be made to the book "Antibodies a laboratory manual" (E. Harlow et al., Cold Spring Harbor Laboratory), pp.471–510. With respect to the details of immunoprecipitation and immunoassay, reference can be made respectively to pp.421–470 and pp.553–612 of the above-mentioned book. Examples of clinical diagnosis using FACS are shown in "Furo-Saitometorii-Handobukku (Flow Cytometry Handbook)", edited by Yoshio TENJIN et al. (published in 1984 by SCIENCE FORUM INC., Japan) (see Section 4: "Furo-Saitometorii-no Rinsho-igaku-eno Ouyo (Application of Flow Cytometry to Clinical Medicine)" of the book). With respect to the staining of cells conducted in FACS, detailed information is shown in "Men-eki-Kenkyu-no Kiso-Gijutu (Basic Techniques for Research in Immunology)", written by Kiyoshi TAKATSU and Shinsuke TAKI (published in 1995 by YODOSHA CO., LTD., Japan), pp.16–61. With respect to the details of the operations of FACS, reference can be made to "Furo-Saitometorii-Handobukku (Flow Cytometry Handbook)", edited by Yoshio TENJIN et al. (published in 1984 by SCIENCE FORUM INC., Japan).

Still further, the present invention provides a method for the diagnosis of an inflammatory disease, which comprises determining the amount of the seven-pass transmembrane receptor C5L2 protein expressed in human leukocytes.

The results of the homology search and the like suggested that the seven-pass transmembrane receptor C5L2 of the present invention greatly participates in immunomodulation in inflammations and infections. Further, it was found that the ratio of the expression of C5L2 protein is especially high in peripheral leukocytes. Based on these observations, studies were made on the possible application of the C5L2 to the diagnosis of an inflammatory disease. First, leukocytes were fractionated into lymphocytes (i.e., T cells, B cells and monocytes) and granulocytes (i.e., neutrophils, eosinophils and basophils), and the ratios of the expression of C5L2 protein in the lymphocytes and in the granulocytes were individually measured by RT-PCR analysis. As a result, a strong expression of a protein having the amino acid sequence of SEQ ID NO:2 was detected in granulocytes. Second, the present inventors focused their attention on rheumatoid arthritis (RA) as a representative inflammatory disease, and further analyses were conducted for examining the relationship between rheumatoid arthritis (RA) and C5L2 gene expression. Particularly, granulocytes were obtained from peripheral blood sampled from patients of rheumatoid arthritis (RA patients) and healthy donors (the total number of the patients and healthy donors was 30 or more), and the granulocytes were analyzed by RT-PCR. Further, the below-mentioned tissues and cells from RA patients were subjected to the RT-PCR analysis: synovial fluid, cells fractionated from synovial fluid, a piece of the synovial membrane, cells obtained by subjecting a piece of the synovial membrane to collagenase treatment, and leukocytes isolated from the above-mentioned cells obtained from the synovial membrane. As a result, a strong expression of C5L2 was detected in granulocytes present in the synovial fluid, and almost no expression of C5L2 was detected in the synovial membrane, which contained almost no granulocytes.

Further, the present inventors considered that it is possible that the ratio of the C5L2 gene expression in sampled body fluids or tissues changes with time during the storage. In order to examine such a possible change in ratio of C5L2 expression, the present inventors conducted the analyses of granulocytes, wherein the granulocytes were isolated from collected human peripheral blood, immediately after the collection of the blood and after storage of the blood for a predetermined period of time, and the isolated granulocytes were analyzed so as to determine how the ratio of the expression of C5L2 gene in granulocytes has changed with time during the storage of the peripheral blood. Specifically, the following analyses were conducted. Blood was collected from healthy donors, and a granulocyte fraction was immediately obtained from a part of the fresh collected blood by buoyant density centrifugation. The remainder of the collected blood was allowed to stand for a predetermined period of time at room temperature, and, then, subjected to buoyant density centrifugation in substantially the same manner as in obtaining the granulocyte fraction from the fresh collected blood, to thereby obtain a granulocyte fraction from the stored blood. The thus obtained granulocyte fractions were individually subjected to RT-PCR using the synthetic primers shown in SEQ ID NOs:9 and 10 to thereby measure the amount of mRNA encoding C5L2 in the granulocytes. As a result, it was found that, in the granulocytes obtained from the peripheral blood of healthy donors, the amount of mRNA encoding C5L2 protein decreased rapidly during the period of time of 0 to 6 hours after the collection of the blood, and then decreased gradually, wherein the decrease in amount of the mRNA continued for 24 hours after the collection of the blood (see FIG. 2).

On the other hand, granulocytes obtained from the peripheral blood of RA patients were also analyzed in substantially the same manner as described above. As a result, it was found that, in the granulocytes obtained from the peripheral blood of RA patients, the amount of the mRNA encoding C5L2 protein did not decrease even when the blood was stored for 24 hours after the collection of the blood.

As apparent from the above, although the granulocytes which are obtained from the peripheral blood of healthy donors immediately after the collection of the blood exhibits a high ratio of the expression of C5L2 gene, the ratio of the C5L2 gene expression decreases rapidly during the storage of the collected blood. Such a phenomenon is not observed in the case of the chemokine receptors CCR4 and CCR5 and, thus, the present inventors have found that this phenomenon is specific to the receptor C5L2 of the present invention. This phenomenon has for the first time been found by the present inventors.

The regulatory mechanism of C5L2 expression in granulocytes is considered to be as follows. The leukocytes in human peripheral blood are composed of 25 to 33% of lymphocytes, 3 to 7% of monocytes, 55 to 60% of neutrophils, 1 to 3% of eosinophils and 0 to 0.7% of basophils (see "Seikagaku Jiten (Dictionary of Biochemistry)" published by TOKYO KAGAKU DOZIN CO., LTD., Japan). As apparent from the above-mentioned composition of the leukocytes in human peripheral blood, neutrophils account for 90% or more of the granulocyte fraction (composed of neutrophils, eosinophils and basophils). Neutrophils participate in the non-specific immune system and they exclude pathogens (mainly bacteria) from the living body by performing various functions (such as adhesion, chemotaxis, phagocytosis and bactericide). A mature neutrophil stays in human peripheral blood for 10 to 16 hours and its life is 2 to 3 days. Mature neutrophils are either those neutrophils circulating in the blood or those neutrophils which are in a form adhering to vascular endothelium (i.e., vascular endothelial cells covering the inside wall of a blood vessel). Under normal conditions, the number of mature neutrophils circulating in the blood and the number of mature neutrophils in a form adhering to vascular endothelium are approximately the same. The mature neutrophils which have been in a form adhering to vascular endothelium will then emigrate into tissues, and such neutrophils are lost as they go out of the tissues and into a space outside the tissues (such as the oral cavity, a gastrointestinal lumen and the internal space of a pulmonary alveolus) or, in the case of some tissues (such as liver, spleen, hypodermal tissue and the like), the neutrophils undergo apoptosis and are then phagocytosed by macrophages. From these facts, it is considered that the average life of mature neutrophils which emigrate into tissues is 1 to 4 days. A mature neutrophil which has emigrated into a tissue does not return to the blood. With respect to the mature neutrophils which migrate to a site of inflammation, the apoptosis of these neutrophils is regulated so that the life of these neutrophils is prolonged. On the other hand, the life of the mature neutrophils which have phagocytosed bacteria is shortened. When a mature neutrophil undergoes apoptosis, its various functions (such as chemotaxis, phagocytosis, morphological change, adhesion, degranulation and production of active oxygen) are lowered (Haslett, C. et al., Chest, 99 (Suppl. 3): 6S, 1991; and Whyte, M. K. et al., J. Immunol., 150, 5124–5134, 1993). Such an onset of neutrophil apoptosis is considered to be caused by a mechanism working for preventing the occurrence of disorders caused by a prolonged activation of neutrophils, which is harmful for the living body.

It is considered that the receptor C5L2 of the present invention is usually expressed on the cells, and that when a disorder (such as an infection or an inflammation) occurs in the living body, the cells expressing C5L2 receptor emigrate into the site of the disorder and act on the disorder. That is the receptor C5L2 is expressed on the cells which are capable of fully functioning at a site of inflammation. For example, in the case of an inflammation which is caused by a bacterial infection, the cells expressing C5L2 emigrate into the site of the inflammation and begin bactericide, wherein, when the bactericide is initiated, the role of C5L2 is completed and the ratio of the expression thereof decreases. In addition, it is considered that when a C5L2 receptor-expressing cell emigrates into a normal tissue (where there is no inflammation) and undergoes apoptosis, the receptor C5L2 disappears from the cell. Collected blood is different, in many respects, from the blood present in a blood vessel of the living body, and, hence, the storage of collected blood is considered to cause a lowering of the cell activity and induction of apoptosis of cells, and, in turn, such occurrence of a lowering of the cell activity and induction of apoptosis is believed to cause a lowering of the ratio of the expression of C5L2 receptor in the cells present in the collected blood.

On the other hand, there is a report that, in mature neutrophils which have migrated to a site of inflammation, the onset of apoptosis is regulated so as to prolong the life of the neutrophils (Watson, R. W. et al., J. Immunol., 158, 945–953, 1997). There is another report that in a patient who is in the inactive stage of Behchet's disease, apoptosis of neutrophils in peripheral blood is suppressed to prolong the life of the neutrophils (Tsuyoshi SAKANE and Mitsuhiro TAKENO, "Kouchuu-kyuu, Kinou teika to kinou koushin (Neutrophils, Hypofunction and hyperfunction)", published in 1998 by MEDICINE AND DRUG JOURNAL CO., LTD. (Iyaku Jaanaru-sha), Japan). Based on these facts, it is considered that the apoptosis of neutrophils in the peripheral blood of patients suffering from an inflammatory disease is also suppressed to prolong the life of the neutrophils. Therefore, it is also considered that, differing from the neutrophils in a blood sample obtained from a healthy person (in which a lowering of cell activity and induction of apoptosis occur), the neutrophils in a blood sample obtained from a patient suffering from an inflammatory disease maintain their activity and, hence, the ratio of the expression of C5L2 in the neutrophils is maintained at a high level. In addition, it is considered that the maintenance of the activity of the neutrophils at a high level for a long period of time is causative of the chronicity of an inflammation.

As a result of the above-described intensive and extensive studies, the present inventors found that, either by determining the change in ratio of the C5L2 gene expression in collected blood, or by determining the ratio of the C5L2 gene expression in collected blood after a predetermined period of time from the blood collection, a useful marker for an inflammatory disease can be obtained. The present invention has been completed, based on these novel findings.

The method of the present invention is useful for the diagnosis of an inflammatory disease in which the hypofunction or hyperfunction of the neutrophils is considered to be one of the causatives. Examples of such inflammatory diseases include rheumatoid arthritis, Behchet's disease, neutrophilic dermatoses (such as Sweet's syndrome and gangrenous pyoderma), adult respiratory distress syndrome (ARDS), ischemic reperfusion injury, septic shock syndrome, systemic inflammatory response syndrome (SIRS) and pancreatitis. Especially, the method of the present invention can be advantageously used for the diagnosis of rheumatism, more advantageously rheumatoid arthritis. The diagnosis of rheumatism using the currently employed marker requires a long-term observation which must be conducted for 6 weeks. On the other hand, when the method of the present invention is used for the diagnosis of rheumatism, the result of the diagnosis can be obtained within only a few days, so that an early diagnosis of rheumatism becomes possible.

The method of the present invention is also useful for the diagnosis of a chronic inflammatory disease. The apoptosis of neutrophils and the subsequent phagocytosis of the neutrophils by macrophages necessarily occur in the normal immunoreaction. Therefore, if the activities of neutrophils are maintained, it follows that the inflammation has become chronic. That is, the activities of neutrophils can be used as an index of the chronicity of the inflammation. Accordingly, the amount of the expressed C5L2 molecules can be used as a marker for a chronic inflammatory disease. Further, with respect to Inflammatory diseases (such as ulcerative colitis and Crohn's disease) in which exacerbation and remission are alternately repeated, whether or not the disease is in the active stage can be determined from the amount of the C5L2 expressed.

It is preferred that the cells used for diagnosis are leukocytes, more advantageously granulocytes. The granulocytes, which are capable of fully functioning in a portion of the body which suffers from inflammation, constantly express C5L2 thereon and, when the activities of granulocytes are lowered, the C5L2 expression is considered to disappear. Therefore, as mentioned above, with respect to the granulocytes in blood collected from a healthy person, the ratio of the expression of the C5L2 decreases with the lapse of time. Especially, when it is intended to distinguish clearly a patient suffering from an inflammatory disease from a healthy person, it is preferred that the granulocytes used for diagnosis are obtained at least six hours before the diagnosis.

In the present invention, there is no particular limitation with respect to the method for determining the amount of the expressed C5L2 protein. For example, there can be mentioned a method in which the amount of mRNA encoding C5L2 is measured, and a method in which the amount of the C5L2 protein present on the cell surface of the cells is measured. An mRNA transcribed from a gene is translated into a protein by an intracellular mechanism. Therefore, the amount of a protein can be estimated from the amount of an mRNA encoding the protein. In the present invention, there is no particular limitation with respect to the method for measuring the amount of mRNA encoding the C5L2 protein, but it is preferred that the amount of the mRNA is measured by reverse transcription PCR (RT-PCR) method. Specifically, in the RT-PCR method, the cDNA encoding C5L2 is synthesized by using a reverse transcriptase, and the synthesized cDNA is amplified using a heat-resistant DNA polymerase and a primer pair which is specific to the C5L2 gene. The amount of the mRNA can be determined from the amount of the amplified cDNA.

Examples of primers used for the RT-PCR method include the DNA fragments of the present invention and derivatives thereof, wherein the DNA fragments are fragmentary sequences (each independently being a sequence of at least 12 contiguous nucleotides, preferably not less than 16 contiguous nucleotides, more preferably not less than 20 contiguous nucleotides) in the nucleotide sequences of SEQ ID NOs:3 and 4, respectively. Specific examples of the primers include synthetic primers shown in SEQ ID NOs:9 and 10. The amount of the mRNA encoding C5L2 can be measured by the method described in Example 11 of the present specification. More specifically, the amount of the mRNA encoding C5L2 protein can be measured by a method in which the mRNA encoding the receptor C5L2 in a sample is detected by using the primers shown in SEQ ID NOs:9 and 10, whereas the mRNA encoding glyceraldehyde 3-phosphate dehydrogenase (G3PDH) in the same sample as mentioned above is detected by using the primers shown in SEQ ID NOs:11 and 12. The amount of the mRNA encoding C5L2 protein is determined in terms of the ratio of the amount of the mRNA based on the amount of the PCR product for G3PDH (i.e., ratio of the expression of C5L2 based on the expression of G3PDH).

In the present invention, there is no particular limitation with respect to the method for measuring the amount of the C5L2 protein present on the cell surface as long as the amount of the C5L2 protein can be measured specifically. For specifically measuring the amount of the C5L2 protein, it is preferred to use an antibody which specifically binds to C5L2 receptor. Examples of such antibodies include an antibody prepared in Example 9 of the present specification, which is prepared using, as an antigen, a peptide which is a fragmentary sequence of at least 5 contiguous amino acid residues in the amino acid sequence of SEQ ID NO:2. Examples of methods for measuring the amount of the C5L2 protein using the above-mentioned antibody include FACS (employed in Example 11 of the present specification) and immunoprecipitation. With respect to examples of clinical diagnosis using FACS, reference can be made to a text book, such as "Furo-Saitometorii-Handobukku (Flow Cytometry Handbook)", Yoshio TENJIN et al. eds. (published in 1984 by SCIENCE FORUM INC., Japan), particularly to Section 4: "Furo-Saitometorii-no Rinsho-igaku-eno Ouyo (Application of Flow Cytometry to Clinical Medicine)" thereof. With respect to the methods for conducting immunoprecipitation and immunoassay, reference can be, respectively, made to pages 421 to 470 and pages 553 to 612 of "Antibodies a laboratory manual" (E. Harlow et al., Cold Spring Harbor Laboratory.

Further, there is a report that an extracellular domain of a seven-pass transmembrane receptor protein (such as CD97) is released from a cell membrane, and solubilized and stably dissolved in a body fluid surrounding a portion suffering inflammation (such as synovial fluid in a joint suffering arthritis) (James X. Gray et al., J. Immunol. 157, 5438–5447, 1996). Therefore, the amounts of the C5L2 protein and the partial peptides thereof which are dissolved in a body fluid, such as blood and synovial fluid, are useful for the diagnosis of an inflammatory disease. Also in this case, it is preferred to use an antibody which specifically binds to C5L2 protein.

Examples of methods for measuring the amount of C5L2 protein include western blotting and FACS.

BEST MODE FOR CARRYING OUT THE INVENTION

Hereinbelow, the present invention will be described in more detail with reference to the following Examples, but they should not be construed as limiting the scope of the present invention.

EXAMPLE 1

Obtainment of a Fragment of a Gene Encoding a Novel Seven-pass Transmembrane Receptor A buffy coat was recovered from 1 liter of peripheral blood of healthy persons, thereby obtaining nucleated cells (leukocytes). The obtained nucleated cells were cultured at 37° C. for 14 days in an atmosphere containing 5% of carbon dioxide to thereby differentiate the nucleated cells into immature dendritic cells. As a medium for culturing the cells, RPMI1640 medium supplemented with 10% of fetal bovine serum (FBS, manufactured and sold by Intergen, U.S.A.), 100 ng/ml of human granulocyte macrophage colony-stimulating factor (GM-CSF), 50 ng/ml of human interleukin 4 (IL-4) and 1× Antibiotic-Antimycotic (i.e., a formulation containing penicillin, streptomycin and amphotericin B in final concentrations of 100 IU/ml, 100 $\mu$g/ml of and 0.25 $\mu$g/ml, respectively) (manufactured and sold under the brand of GIBCO BRL™, U.S.A.). By culture under the above-mentioned conditions, 1×10$^7$ immature dendritic cells were obtained from peripheral leukocytes.

The obtained immature dendritic cells were collected and suspended in 30 ml of PBS (Phosphate Buffered Saline). mRNAs were extracted from the immature dendritic cells in the resultant suspension by using Quick Prep mRNA Purification Kit (manufactured and sold by Pharmacia Biotech AB, Sweden) in accordance with the protocol attached thereto, except that the second column purification was not conducted. Next, using 1 $\mu$g of the extracted mRNAs, cDNAs were synthesized from the 9 mRNAs by using SuperScript Choice System for cDNA Synthesis (manufactured and sold by Life Technologies, Inc., U.S.A.) in accordance with the protocol attached thereto. The synthesized cDNAs were converted into double stranded cDNAs (dsDNAs). The obtained dsDNAs were subjected to phenol/chloroform extraction and subsequent ethanol precipitation, thereby precipitating the dsDNAs. The precipitate (dsDNAs) was dissolved in 40 $\mu$l of sterilized water, and the resultant solution was used as a cDNA sample.

The cDNA sample was amplified by polymerase chain reaction (PCR). Specifically, to 2 $\mu$l of the cDNA sample were added 0.5 $\mu$l of TaKaRa Taq (code No: R001A) (manufactured and sold by TAKARA SHUZO CO., LTD., Japan) as a DNA polymerase (wherein the final concentration of the DNA polymerase became 5 U/$\mu$l), 5 $\mu$l of 10×PCR buffer (attached to TaKaRa Taq), 4 $\mu$l of dNTP mixture (the concentration of each nucleotide: 2.5 mM) and synthetic oligonucleotides having the sequences of SEQ ID NOs:5 and 6 as primers (each in an amount of 200 pmol). Then, sterilized water was added to the resultant mixture so as to adjust the final volume of the mixture to 50 $\mu$l.

The resultant mixture was subjected to 30 cycles of PCR using TaKaRa PCR Thermal Cycler 480 (manufactured and sold by TAKARA SHUZO CO., LTD., Japan) to thereby obtain a mixture of PCR products. Specifically, each of the first 5 cycles was conducted under the following conditions:

1 minute at 95° C., 2 minutes at 40° C. and 3 minutes at 72° C.; and each of the remaining 25 cycles was conducted under the following conditions: 1 minute at 95° C., 2 minutes at 50° C. and 3 minutes at 72° C. A part of the obtained mixture of PCR products was subjected to electrophoresis on 1.5% agarose gel, and the result of the electrophoresis confirmed that cDNAs of about 700 bp were amplified by PCR. The band corresponding to the 700 bp cDNA fragments was cut-out from the agarose gel and subjected to purification using GENECLEAN II Kit (manufactured and sold by BIO 101, Inc., U.S.A.) to thereby obtain purified cDNA fragments.

The purified 700 bp cDNA fragments were subcloned into plasmid vectors pCR2.1 (manufactured and sold by Invitrogen Corporation, U.S.A.) using TA cloning kit (manufactured and sold by Invitrogen Corporation, U.S.A.) to thereby obtain recombinant plasmids. E. coli One Shot Competent Cells (manufactured and sold by Invitrogen Corporation, U.S.A.) were transformed with the obtained recombinant plasmids. The resultant transformants (i.e., clones) were isolated using ampicillin-resistance as an index. The plasmids contained in the transformants were purified using Wizard™ Minipreps (manufactured and sold by Promega Corporation, U.S.A.) in accordance with the protocol attached thereto, thereby obtaining purified recombinant plasmids. The fact that the above-mentioned PCR products were inserted into the purified plasmids was confirmed by a method in which the purified plasmids are digested with a restriction enzyme EcoRI, and the DNA fragments of about 700 bp which have been cut-out from the plasmids are detected.

With respect to the purified recombinant plasmids, the nucleotide sequences of the cDNA fragments inserted into the plasmids were determined using a fluorescence sequencer (manufactured and sold by Applied Biosystems Inc., U.S.A.). The sequence sample used for the sequence determination was prepared using PRISM, Ready Reaction Dye Terminator Cycle Sequencing Kit (manufactured and sold by Applied Biosystems Inc., U.S.A.). Specifically, 9.5 $\mu$l of a stock solution for reaction, 4.0 $\mu$l of T7 promoter primer (0.8 pmol/$\mu$l) (manufactured and sold under the brand GIBCO BRL™, U.S.A.) and 6.5 $\mu$l of a solution containing a template DNA for sequencing (0.16 $\mu$g/$\mu$l) were mixed together in a 0.5 ml microtube to thereby obtain an aqueous mixture. Subsequently, 100 $\mu$l of mineral oil was added to the aqueous mixture so that the resultant mixture consisted of an aqueous phase (as a lower layer) and a mineral oil phase (as an upper layer) formed on the surface of the aqueous phase. The obtained mixture was subjected to 25 cycles of PCR by means of TaKaRa PCR Thermal Cycler 480, wherein each cycle was conducted under the following conditions: 30 seconds at 96° C., 15 seconds at 55° C. and 4 minutes at 60° C., and wherein, after completion of the 25 cycles of PCR, the resultant reaction mixture was incubated at 4° C. for 5 minutes. 80 $\mu$l of sterilized, purified water was added to and mixed well with the thus obtained reaction mixture. The resultant mixture was subjected to centrifugation to thereby separate an aqueous phase from the mixture. The obtained aqueous phase (aqueous solution) was subjected to phenol/chloroform extraction 3 times, and then to ethanol precipitation at room temperature thereby precipitating a DNA. The precipitated DNA was dried and, then, dissolved in 4 $\mu$l of formamide containing 10 mM of EDTA. The resultant DNA solution was heated at 90° C. for 2 minutes to denature the DNA (i.e., melting the dsDNA into ssDNA) and subsequently cooled in an ice bath, thereby obtaining a DNA sample for sequencing.

The determination of the nucleotide sequences of the cDNA fragments introduced into the plasmid vectors was conducted with respect to approximately 250 clones. One of the sequenced clones contained a nucleotide sequence corresponding to the 235th to 852nd nucleotides of SEQ ID NO:1. This nucleotide sequence was subjected to a homology search in GenBank (release 106.0, April, 1998), and as a result, this sequence was found to be homologous to the known seven-pass transmembrane receptors.

EXAMPLE 2

Obtainment of the Whole Length Gene Encoding the Novel Seven-pass Transmembrane Receptor A human cDNA library derived from human placental tissue (manufactured and sold by CLONTECH Laboratories, Inc., U.S.A.) was screened by plaque hybridization, thereby isolating clones containing the whole length cDNA encoding the seven-pass transmembrane receptor of the present invention. Specifically, 1×10$^6$ bacteriophages (which constitute the cDNA library) were plated in a usual manner and incubated until bacteriophage plaques appeared on the plate (this plate was used as a master plate). Then, the bacteriophages contained in the plaques present on the master plate were transferred to a nylon filter (Hybond N+; manufactured and sold by Amersham International, England). The nylon filter carrying the bacteriophages was placed on a filter paper saturated with an alkali buffer (1.5 M NaCl/0.5 M NaOH), and allowed to stand for 5 minutes, to thereby conduct an alkali treatment of the phages transferred to the filter. Subsequently, the nylon filter was removed from the above-mentioned filter paper, and placed on a filter paper saturated with a neutralizing buffer (1.5 M NaCl/0.5 M Tris-HCl, pH 7.5), and allowed to stand for 5 minutes, to thereby neutralize the alkali-treated phages. This neutralization treatment was conducted twice. After the neutralization treatment, the nylon filter was washed twice by keeping it in a 2×SSC solution (wherein a 1×SSC solution is composed of 0.15 M NaCl and 15 mM citric acid (pH 7.0)) for 5 minutes with shaking, and then, the washed filter was air-dried. The dried filter was irradiated with UV light by means of UV Crosslinker CL-1000 (manufactured and sold by Funakoshi Co., Ltd., Japan), wherein the intensity of the UV irradiation was 1,200×160 $\mu$J/cm$^2$, to thereby immobilize the phage DNAs to the filter.

Next, a probe was prepared by labeling the fragment of a gene obtained in Example 1 (i.e., the DNA fragment encoding a seven-pass transmembrane receptor) with a radioisotope $^{32}$P. Specifically, the recombinant plasmid prepared in Example 1 (i.e., the vector pCR2.1 having inserted therein the EcoRI fragment of a gene encoding a seven-pass transmembrane receptor) was digested with a restriction enzyme EcoRI, to thereby obtain fragments including the EcoRI fragment (about 700 bp). The obtained fragments were resolved by electrophoresis on 0.8% agarose gel. The band corresponding to the 700 bp DNA fragment was cut-out from the agarose gel and subjected to purification using GENECLEAN II Kit (manufactured and sold by BIO 101, Inc., U.S.A.) to thereby obtain a purified EcoRI fragment. The obtained fragment was labeled with [$\alpha$-$^{32}$P] dCTP (Code AA 0005) (manufactured and sold by Amersham International, England) by using Megaprime DNA labeling system (Code RPN1607) (manufactured and sold by Amersham International, England) in accordance with the protocol attached thereto, thereby obtaining a labeled DNA. The labeled DNA was purified using Quick Spin™ Column Sephadex™ G-50 (manufactured and sold by Boehringer Mannheim Corporation, Germany). The resultant purified DNA was heated in a boiling water bath for 5 minutes and then cooled in an ice bath for 2 minutes, thus obtaining a probe for hybridization.

The obtained $^{32}$P-labeled probe (i.e., a $^{32}$P-labeled DNA fragment of a gene encoding a receptor) was hybridized with the phage DNAs immobilized on the filter. Specifically, the filter having the phage DNAs immobilized thereon was immersed in a hybridization solution containing 6×SSC solution, 5× Denhardt's solution, 0.5% of SDS (sodium dodecyl sulfate) and 100 µg/ml salmon sperm DNA, and the filter was incubated therein at 65° C. for 2 hours with shaking. Subsequently, the probe was added to the hybridization solution and the filter was further incubated at 65° C. for 16 hours with shaking, to thereby hybridize with each other the probe and the DNAs immobilized on the filter.

The filter carrying the resultant hybridization product was washed three times by immersing the filter in a washing solution (2×SSC solution containing 0.1% SDS) at room temperature, and further washed with the same washing solution for 15 minutes at room temperature. The washed filter was subjected to autoradiography at −85° C. Several dark dots caused by exposure to strong radiation were detected in the resultant autoradiogram. From the above-mentioned master plate having bacteriophage plaques thereon, those bacteriophage plaques respectively corresponding to the above-mentioned dark dots were selected, and individually replaced, and then screened in substantially the same manner as mentioned above, to thereby obtain bacteriophage plaques each corresponding to an isolated, completely single type of phage clone.

Among the isolated phage clones, two clones were used for determining the whole length nucleotide sequence of the gene encoding the novel seven-pass transmembrane receptor. Specifically, with respect to each phage clone, a phage preparation containing phages in an amount of $10^9$ pfu (plaque forming unit) was prepared. The phage DNA was purified from each of the phage preparations by using Wizard™ Lambda Preps (manufactured and sold by Promega Corporation, U.S.A.). The purified DNAs were individually digested with EcoRI, thereby obtaining EcoRI fragments of the phage DNAs. A plasmid vector pBluescript II KS(+) (manufactured and sold by Stratagene Cloning Systems, U.S.A.) was separately digested with EcoRI, and the above-obtained EcoRI fragments of the phage DNAs were individually inserted into the digested plasmid vectors pBluescript II KS(+) at the EcoRI site thereof, to thereby obtain recombinant plasmid clones containing phage DNAs.

The nucleotide sequences of the obtained clones were analyzed using a fluorescence sequencer. As a result, the whole length nucleotide sequence of the gene encoding a novel seven-pass transmembrane receptor, namely the nucleotide sequence of SEQ ID NO:3, was determined. The present inventors designated this novel seven-pass transmembrane receptor as "C5L2". The portion of SEQ ID NO:3 which encodes the C5L2 protein is shown in SEQ ID NO:1. Further, the plasmid containing the DNA encoding the C5L2 protein was designated as "pBSC5L2".

EXAMPLE 3

Northern Blotting Analysis

In Example 2 above, the whole length nucleotide sequence of the gene encoding the human seven-pass transmembrane receptor C5L2 was obtained. With respect to this receptor, the mRNA expressions in various organs were analyzed by northern blotting. In the northern blotting analysis, filters used were Multiple Tissue Northern (MTN) Blots filters (catalog numbers: #7757-1, #7759-1, #7760-1 and #7767-1) (each manufactured and sold by CLONTECH Laboratories, Inc., U.S.A.), to which the RNAs derived from various organs are fixed. The NaeI-EcoRI restriction fragment of the 3'-terminal region of the C5L2 gene was used as a probe after being labeled with $^{32}$P in the same manner as mentioned in Example 2. The above-mentioned filters were immersed in a hybridization solution obtained by mixing 5×SSPE solution (1×SSPE solution (pH 7.4) is composed of 0.15 M NaCl, 10 mM NaH$_2$PO$_4$ and 1 mM EDTA), 10× Denhardt's solution, 2% SDS, a 50% formamide solution and 100 µg/ml salmon sperm DNA, and then, the filters were incubated at 50° C. for 2 hours with shaking. Subsequently, the probe was added to the hybridization solution and, then, the filters were further incubated at 50° C. for 16 hours with shaking to thereby hybridize the probe with the mRNAs.

The filters were washed twice with 0.1×SSC solution containing 0.1% SDS at 50° C. for 20 minutes and, then, further washed once at 60° C. for 20 minutes. The resultant washed filters were subjected to autoradiography at −85° C. In the resultant autoradiogram, a high intensity band was detected at the position of about 2.4 kb (which corresponds to the size of C5L2) in each of peripheral leukocytes and spleen. In each of bone marrow, lymph nodes, spinal cord, kidney, liver, lung, placenta and heart, a low intensity band was detected at the above-mentioned position of about 2.4 kb. Further, in each of peripheral leukocytes, spleen and testis, a band was also detected at the position of slightly larger than 2.4 kb. On the other hand, a band was not detected at the above-mentioned positions in brain, skeletal muscle, pancreas, thymus, prostate gland, stomach, thyroid gland, trachea, adrenal gland, fetal brain, fetal lung, fetal liver and fetal kidney.

The band at the position of about 2.4 kb was also detected in immature dendritic cells, but not detected in mature dendritic cells. These results show that the expression of C5L2 disappears during the maturation of dendritic cells.

EXAMPLE 4

Preparation of a Recombinant DNA Expressing the Seven-pass Transmembrane Receptor C5L2

The plasmid clone (pBSC5L2) containing the whole length C5L2 gene isolated in Example 2 was used as a template for amplifying the C5L2 gene by PCR. High Fidelity Taq polymerase (manufactured and sold by Boehringer Mannheim Corporation, Germany) was used as a polymerase for the PCR. The PCR was conducted as follows.

To 1 µl of 5 ng/µl pBSC5L2 solution were added 0.5 µl of the High Fidelity Taq polymerase, 5 µl of 10× buffer (attached to the High Fidelity Taq polymerase) and 4 µl of 2.5 mM dNTP mixture (manufactured and sold by TAKARA SHUZO CO., LTD., Japan). To the resultant mixture were added 20 pmol of each of PCR primers which are an oligonucleotides having a sequence shown in SEQ ID NO:7 (i.e., a sequence obtained by adding the spacer sequence "gggg" and the restriction enzyme HindIII recognition site "aagctt" to the 5'-end of a sequence corresponding to the 1st to 22nd nucleotides of SEQ ID NO:1) and an oligonucleotide having a sequence shown in SEQ ID NO:8 (i.e., a sequence obtained by adding the spacer sequence "ggga" and the restriction enzyme SacII recognition site "ccgcgg" to the 5'-end of a sequence corresponding to the 206th to 225th nucleotides of SEQ ID NO:4). Then, sterilized water was added to the mixture so as to adjust the final volume of the mixture to 50 µl.

The resultant mixture was subjected to 20 cycles of PCR by means of TaKaRa PCR Thermal Cycler 480, wherein each cycle was conducted under the following conditions: 1 minute at 96° C., 1 minute at 60° C. and 2 minutes at 72° C., and wherein, after completion of the 20 cycles of PCR, the resultant reaction mixture was incubated at 72° C. for 7 minutes. A part of the resultant reaction mixture was electrophoresed on 0.8% agarose gel. The result of the electrophoresis showed that cDNA of about 1,150 bp was amplified by PCR. The amplified cDNA was recovered in accordance with the conventional methods, namely, a method in which the reaction mixture obtained by the above PCR was subjected to phenol/chloroform extraction, followed by the ethanol precipitation, and the amplified DNA was recovered as a precipitate. The obtained DNA was dissolved in sterilized water, thereby obtaining a DNA solution. Next, the obtained DNA solution was successively digested with HindIII and SacII, thereby obtaining a HindIII-SacII restriction fragment. The digested DNA solution was electrophoresed on 0.8% agarose gel to resolve the resultant DNA fragments. The band of the HindIII-SacII restriction fragment was cut-out from the gel and was subjected to purification using GENECLEAN II Kit to thereby obtain a purified HindIII-SacII fragment. The plasmid vector pcDNA3.1/Myc-His(+)B was also digested with HindIII and SacII, and the resultant plasmid from which the HindIII-SacII fragment had been cut-out was purified. The HindIII-SacII restriction fragment of C5L2 was inserted into the cut-out portion of the plasmid pcDNA3.1/Myc-His(+)B, and ligated using DNA Ligation Kit Ver.2 (manufactured and sold by TAKARA SHUZO CO., LTD., Japan) to thereby obtain a C5L2 recombinant plasmid. *E. coli* (DH5) competent cells (manufactured and sold by TAKARA SHUZO CO., LTD., Japan) were transformed with the obtained recombinant plasmid. The resultant transformants (i.e., clones) were isolated using ampicillin resistance as an index. The plasmid contained in the transformants was purified by means of Wizard™ Minipreps (manufactured and sold by Promega Corporation, USA) in accordance with the protocol attached thereto. The insertion of the C5L2 gene into the plasmid vector was confirmed by a method in which the purified plasmid is digested with the restriction enzymes HindIII and SacII and a DNA fragment of about 1,150 bp (which has been cut-out from the recombinant plasmid) is detected. The recombinant plasmid DNA comprising the C5L2 gene was named "pcDNAC5L2".

An international deposit of the transformant obtained by introducing pcDNAC5L2 into *E. coli* (DH5), namely, *E. coli*: DH5-pcDNAC5L2 (Deposit number: FERM BP-6833), was made with National Institute of Bioscience and Human-Technology, Agency of Industrial Science and Technology in Japan on Sep. 1, 1998.

EXAMPLE 5

Transformation of Cells with the Recombinant DNA and Expression of the Recombinant DNA The cells of 293 cell line (ATCC No. CRL-1573, available from Dainippon Pharmaceutical Co., Ltd., Japan) were transformed (transfected) with the recombinant DNA (pcDNAC5L2) prepared in Example 4 to thereby obtain pcDNAC5L2 transformants. Specific conditions for the transformation were as follows.

The cells of 293 cell line were incubated in MEM Earle liquid medium (MEM with Earles Salts, catalog number: 12-102-54CN) (manufactured and sold by Dainippon Pharmaceutical Co., Ltd., Japan) supplemented with 10% horse serum (catalog number: 2921149) (manufactured and sold by ICN Biomedicals, Inc., USA) and 1% (vol/vol) Penicillin-Streptomycin solution (catalog number: 16-70D-49DN) (manufactured and sold by Dainippon Pharmaceutical Co., Ltd., Japan) under conditions wherein the temperature was 37° C., the carbon dioxide concentration was 5% and the humidity was 100%. The transformation of the cells was conducted by calcium phosphate co-precipitation method using Calcium Phosphate Transfection Kit (catalog number: IV2780-1) (manufactured and sold by Invitrogen Corporation, USA) in accordance with the protocol attached thereto. As a control, the cells of 293 cell line were transformed with an empty vector (i.e., pcDNA3.1/Myc-His(+)B vector). Each of the recombinant DNA and the empty vector was used in an amount of 5 µg per plate (diameter: 35 mm).

With respect to the thus obtained transformants (i.e., the pcDNAC5L2 transformants or the control), the cell membrane fraction thereof was prepared as follows.

The transformants were incubated for 48 to 72 hours. The incubated cells were washed with PBS and, then, 1 ml/plate of EDTA-containing PBS (EDTA concentration: 0.01%) was added to the washed cells. Using Cell Scraper-L (catalog number: MS-93300) (manufactured and sold by Sumitomo Bakelite Co., Ltd., Japan), the cells were scraped off from the plate and washed twice with PBS. The washed cells were suspended in 0.5 ml of 25 mM HEPES solution (pH 7.4) containing Complete™ Protease Inhibitor Cocktail Set (manufactured and sold by Boehringer Mannheim Corporation, Germany), and the resultant cell suspension was transferred to a microtube. The cell suspension was homogenized using a syringe equipped with a 26G needle, and the resultant homogenate was subjected to centrifugation at 3,000 rpm for 5 minutes at 4° C. by means of a microtube centrifuge (Model: MRX-150) (manufactured and sold by Tomy Co., Ltd., Japan). The supernatant was collected and subjected to further centrifugation at 15,000 rpm for 15 minutes to thereby obtain a precipitate containing cell membrane. The obtained precipitate was washed twice with HMS solution (containing 50 mM HEPES (pH 7.4), 5 mM $MgCl_2$ and 150 mM NaCl) and, then, suspended in 100 µl of the HMS solution. The resultant suspension was used as a cell membrane fraction preparation in the following experiment.

The expression of the seven-pass transmembrane receptor C5L2 protein was confirmed by western blotting using the cell membrane fraction preparation. Specifically, 2-mercaptoethanol was added to the membrane fraction preparation, and the resultant mixture was heated in a boiling water bath for 5 minutes to thereby conduct the reduction treatment. The treated membrane fraction preparation was subjected to SDS-PAGE (SDS-polyacrylamide gel electrophoresis) using a 5 to 15% gradient gel. Rainbow marker (high range) (manufactured and sold by Amersham International, England) was used as a molecular weight marker. After SDS-PAGE, the proteins resolved in the polyacrylamide gel were transferred to Immun-Blot PVDF membrane (a membrane for use in immunoblotting) (manufactured and sold by Bio-Rad Laboratories, USA) by means of Minitransblot cell (manufactured and sold by Bio-Rad Laboratories, U.S.A.). The resultant membrane was immersed in BLOCKACE (manufactured and sold by Dainippon Pharmaceutical Co., Ltd., Japan) solution and then, incubated at 4° C. overnight with shaking to thereby block the membrane. The resultant membrane was washed with TBS-T (containing 20 mM Tris-HCl (pH 7.6), 137 mM NaCl and 0.1% Tween 20), and the western blotting was conducted by means of ECL western blotting detection system (manufactured and sold by Amersham International, England) in accordance with the protocol attached thereto. An anti-C5L2 antiserum produced in Example 9 below was used as a primary antibody and an anti-rabbit Ig donkey antibody labeled with peroxidase (manufactured and sold by Amersham International, England) was used as a secondary antibody. Each of the antibodies was individually reacted with the proteins transferred to the membrane at room temperature for 1 hour. After the reaction with each antibody, the membrane was washed three times with TBS-T at room temperature for 10 minutes with shaking. The resultant membrane was immersed in a reaction solution of ECL western blotting detection system for 5 minutes and, then, the membrane was taken out of the reaction solution and exposed to an X-ray film. As a result, a band of about 38 to 42 kD was detected in the membrane fraction of the pcDNAC5L2-transformed cells, whereas such a band was not detected in the membrane fraction of the cells transformed with the empty vector (pcDNA3.1/Myc-His(+)B vector).

EXAMPLE 6

Screening of a Ligand

The cell membrane fractions were prepared from the 293 cells (i.e., cells of 293 cell line) transformed with pcDNAC5L2 (i.e., C5L2 transformants) and the 293 cells transformed with pcDNA3.1/Myc-His(+)B vector (i.e., control) in substantially the same manner as in Example 5. As a ligand candidate compound, CGS21680 which is known as a specific agonist for $A_{2A}$ receptor (one of the GPCRs (G-protein coupled receptors)) was used. With respect to each of the prepared membrane fractions, the binding between the C5L2 protein and the ligand candidate compound was examined as follows. To 50 µl of the membrane fraction were added 50 µl of radio-labeled CGS21680 solution (catalog number: NET-1021, manufactured and sold by DuPont NEN, U.S.A.) and 50 µl of PBS, and the resultant mixture (volume: 150 µl, the final concentration of CGS21680: 100 nM) was stirred so as for the C5L2 protein in the membrane fraction to be contacted with the ligand candidate compound. Then, the resultant mixture was incubated at 37° C. for 30 minutes. Subsequently, the mixture was centrifuged at 15,000 rpm for 15 minutes at room temperature by means of a microtube centrifuge to thereby separate the candidate compound which did not bind to the C5L2 protein (i.e., unbound candidate compound). From the resultant centrifuged mixture, 1 µl of a supernatant containing the unbound candidate compound was sampled, and added to and mixed with 10 ml of a scintillation cocktail (ECONOFLUOR-2, manufactured and sold by DuPont NEN, U.S.A.), thereby preparing a sample for liquid scintillation analysis. Subsequently, the radioactivity of the prepared sample was measured by means of a scintillation counter (Beckman LS6000LL, manufactured and sold by Beckman Instruments, Inc., U.S.A.). The amount of the unbound candidate compound was determined from the measured radioactivity.

As a result, no difference in the radioactivity was observed between the sample prepared using the C5L2 transformants and that prepared using the control cells.

EXAMPLE 7

Screening of a Ligand

CHO cells (ATCC number:. CCL-61, available from Dainippon Pharmaceutical Co., Ltd., Japan) were transformed with pcDNAC5L2 constructed in Example 4. The CHO cells were cultured at 37° C. in an atmosphere containing 5% of carbon dioxide using F-12 nutrient mixture (Ham's F-12, catalog number: 11765-047, manufactured and sold under the brand of GIBCO BRL™, U.S.A.) containing 10% FBS (catalog number: 10099-141, manufactured and sold under the brand of GIBCO BRL™, U.S.A.) and 1% (vol/vol) of Penicillin-Streptomycin. The transformation was conducted by the calcium phosphate co-precipitation method using Calcium Phosphate Transfection Kit in accordance with the protocol attached thereto. DNA was used in an amount of 5 µg per plate (diameter: 35 mm).

After the transformation, the cells were transferred to a medium containing 400 µg/ml Geneticin (catalog number: 11811-023, manufactured and sold under the brand of GIBRO BRL™, U.S.A.) in various cell numbers. The cells were grown for approximately two weeks and the grown cells were used in the experiment below as C5L2 protein-expressing CHO cells.

Using the above-mentioned C5L2 protein-expressing CHO cells, the chemotaxis of the cells was observed. As a sample material containing a ligand candidate substance, an LPS (lipopolysaccharide)-administered rat serum was used, which had been prepared as follows. *Salmonella minnesota* Re 595-derived LPS (manufactured and sold under the brand of SIGMA™, U.S.A.) was suspended in a physiological saline, wherein the LPS was used in an amount such that the final concentration thereof became 1 mg/ml. The resultant suspension was sonicated by means of a sonicator (manufactured and sold by Branson, Japan) to thereby obtain a transparent solution. The obtained solution was diluted ten-fold with the physiological saline and 400 µl of the diluted solution was intravenously administered to a 7-week-old Wistar rat (bought from NIPPON BIO-SUPP CENTER, Japan) at the tail thereof. About two hours after the administration, the rat was etherized and laparotomized, and then, blood was collected from the heart thereof. The collected blood was centrifuged at 13,000 rpm for 15 minutes at 4° C. by means of a microtube centrifuge. From the resultant centrifuged blood, a supernatant was separated and used as a sample material containing a ligand candidate substance.

A 96-well microplate (catalog number: FE-2300-02, manufactured and sold by Funakoshi Co., Ltd., Japan) and a frame filter (pore size: 8 µm) (catalog number: FE-2340-08, manufactured and sold by Funakoshi Co., Ltd., Japan) were set in a 96-well microplate chamber (catalog number: FE-2292-96, manufactured and sold by Funakoshi Co., Ltd., Japan), such that the microplate chamber is separated into a lower compartment and an upper compartment through the frame filter, wherein the microplate is fittedly accommodated in the lower compartment. The frame filter had been treated with 15 µg/ml of fibronectin (manufactured and sold under the bland of SIGMA™, U.S.A.) in PBS before being set in the microplate chamber.

The sample material was diluted ten-fold with RPMI1640 medium (catalog number: 22400-071, manufactured and sold under the brand of GIBCO BRL™, U.S.A.) containing 0.15% BSA (bovine serum albumin), and the resultant solution was added to the lower compartment of the microplate chamber. The C5L2 protein-expressing CHO cells suspended in RPMI1640 medium containing 0.15% BSA was added to the upper compartment of the micro-plate chamber, and then, the microplate chamber was incubated at 37° C. for 5 hours under an atmosphere containing 5% of carbon dioxide, to thereby contact the sample material with the C5L2 protein expressed on the cells. Subsequently, the frame filter was removed from the microplate chamber and the cells attached to the filter were fixed, and then stained for the observation using a microscope. As a result, the chemotaxis of the cells was observed, and hence, it has become apparent that the LPS-administered rat serum contains a ligand candidate compound.

EXAMPLE 8

Screening of a Substance which Antagonizes a Ligand

A chemotaxis Assay was Conducted with respect to the CHO cells transformed with C5L2. First, the chemotaxis of the cells was observed in substantially the same manner as in Example 7 (that is, by adding the serum of an LPS-administered rat to C5L2 protein-expressing CHO cells (transformants) prepared in Example 7). Next, the chemotaxis of the cells was observed in substantially the same manner as in Example 7 except that NECA (5'-(N-ethylcarboxyamide)adenosine) (manufactured and sold under the brand of SIGMA™, U.S.A.), which is an antagonist of GPCRs, was added to each of the media in the upper and lower compartments of the 96-well microplate chamber, wherein NECA was used in an amount such that the final concentration thereof became 100 $\mu$M, and wherein NECA was employed as an antagonist candidate substance (suspected antagonist) against a ligand. The chemotaxis of the cells in the absence of the antagonist candidate substance against a ligand was compared with that in the presence of the antagonist candidate substance against a ligand. As a result, no difference was observed between the chemotaxis of the cells in the absence of the antagonist candidate substance and the chemotaxis of the cells in the presence of the antagonist candidate substance.

EXAMPLE 9

Preparation of Antibodies which Recognize the C5L2 Protein

A peptide having the 6th to 32nd amino acids in the amino acid sequence of SEQ ID NO:2 was synthesized, except that a cysteine residue was added to the N-terminus of the peptide so as to enhance the ability of the peptide to undergo a binding reaction with a carrier protein. Subsequently, KLH (Keyhole Limpet Hemocyanin) and OVA (Ovalbumin) were conjugated with the synthesized peptide by using Inject Activated Immunogen Conjugation Kit with KLH and OVA (Cat. No. 77108, manufactured and sold by PIERCE CHEMICAL COMPANY, U.S.A.), thereby obtaining an immunogen. A rabbit was immunized with the obtained immunogen. Whole blood was collected from the immunized rabbit after measuring the antibody titer of the blood of the rabbit, and antiserum was prepared from the collected blood. Rabbit anti-human C5L2 protein polyclonal antibodies were purified from the prepared antiserum by using Econo-Pac Serum IgG Purification Kit (manufactured and sold by Bio-Rad Laboratories, U.S.A.) in accordance with the instruction manual attached thereto.

In addition, further antibody was prepared in the following manner. A peptide having the 1st to 23rd amino acids in the amino acid sequence of SEQ ID NO:2 was synthesized. By using the synthesized peptide, an immunogen for immunizing a rabbit was prepared in the same manner as described above, and a rabbit was immunized with the obtained immunogen, and then, an antiserum was prepared from the immunized rabbit in the same manner as described above. From the prepared antiserum, polyclonal antibody proteins were partially purified by ammonium sulfate precipitation, and the resultant precipitate was subjected to dialysis against PBS thereby performing a buffer exchange with PBS and obtaining a partially purified antiserum. The peptide synthesized above was immobilized on AF-Tresyl TOYOPEARL Gel (manufactured and sold by Tosoh Corp., Japan) in accordance with the instruction manual attached thereto, and then, an affinity column was prepared using the above-mentioned gel having the peptide immobilized thereon. A part of the partially purified antiserum was applied to the column, thereby allowing the antibody proteins (namely immunoglobulins) contained in the antiserum to bind to the peptide immobilized on the gel. Subsequently, the immunoglobulins were eluted from the column with 1.0 M glycine/hydrochloric acid buffer (pH 2.5), thereby obtaining an immunoglobulin solution. The immunoglobulin solution was subjected to dialysis against PBS thereby performing a buffer exchange with PBS, thus obtaining an affinity-purified anti-C5L2 antiserum solution containing high affinity anti-C5L2 immunoglobulins. 0.3 mg of the proteins (including immunoglobulins) in the affinity-purified anti-C5L2 antiserum solution was reacted with EZ-Link (Cat. No. 21338, manufactured and sold by PIERCE CHEMICAL COMPANY, U.S.A.) in accordance with the instruction manual attached thereto, thereby biotinylating the proteins including the immunoglobulins.

EXAMPLE 10

Detection of the Expression of C5L2 Protein in Dendritic Cells by Means of a Flow Cytometer Dendritic cells were obtained from peripheral blood as follows. Peripheral blood was collected from healthy persons, and a layer of mononuclear cells was recovered using Ficoll. The recovered mononuclear cells were cultured in a culture dish (manufactured and sold under the brand of FALCON™), and the cultured mononuclear cells adhering to the dish were recovered. The recovered mononuclear cells were cultured at 37° C. in an atmosphere containing 5% carbon dioxide, wherein the culture was conducted either for 7 days to thereby differentiate the mononuclear cells into immature dendritic cells or for 11 days to thereby differentiate the mononuclear cells into mature dendritic cells. Specifically, RPMI1640 medium containing 10% FBS (manufactured and sold by Intergen, U.S.A.) and 1× Antibiotic-Antimycotic was used as a culture medium, wherein, with respect to the culture for the first 7 days (for obtaining immature dendritic cells), the culture medium was used in a form containing added thereto human GM-CSF (final concentration: 100 ng/ml) and human IL-4 (final concentration: 50 ng/ml) as stimulating factors, and wherein, with respect to the culture for the 8th to 11th days from the start of the culture (for obtaining mature dendritic cells), the culture medium was used in a form further containing added thereto human TNF-α (final concentration: 10 ng/ml) in addition to the above-mentioned human GM-CSF and human IL-4

With respect to the immature and mature dendritic cells obtained by the above-mentioned method, C5L2 protein expressed on the cell surface was detected by means of a flow cytometer. For performing the detection, the dendritic cells were labeled as follows. The cells were suspended in PBS containing mouse normal serum (manufactured and sold by DAKO, Denmark), thereby obtaining a cell suspension. A biotinylated anti-C5L2 antiserum (as a primary label) was added to the cell suspension and the resultant mixture was incubated at 4° C. for 30 minutes to thereby effect a reaction for primary-labeling the dendritic cells. The cells for a negative control were prepared by labeling the dendritic cells with a biotinylated anti-rabbit IgG anti-body (as a primary label). The primary-labeled cells were washed with PBS twice. Subsequently, FITC-labeled avidin (manufactured and sold by Beckton Dickinson Company, U.S.A.) (as a secondary label) was added to the washed cells, and the resultant mixture was incubated at 4° C. for 30 minutes to thereby effect a reaction for secondary-labeling the dendritic cells with avidin. Subsequently, the cells were washed again to thereby obtain labeled cells. The fluorescence intensity of the labeled cells was measured by means of FACS Calibur (manufactured and sold by Beckton Dickinson Company, U.S.A.).

The results obtained by measuring the expression of C5L2 protein on the cell surface of the dendritic cells by means of FACS are shown in FIG. 1. As seen from FIG. 1, the expression of C5L2 protein was high in immature dendritic cells as compared to that in mature dendritic cells. Therefore, it has become apparent that the novel seven-pass transmembrane receptor C5L2 protein of the present invention is highly expressed in immature dendritic cells, but the expression thereof is decreased in mature dendritic cells.

EXAMPLE 11

Expression of C5L2 Gene in Peripheral Blood of a Rheumatoid Arthritis (RA) Patient (1) Preparation of Peripheral Blood Mononuclear Leukocytes and Granulocytes Peripheral blood cells in blood were fractionated as follows. 10 ml of human peripheral blood (to which heparin had been added in an amount such that the final heparin concentration became 20 U/ml) was diluted three-fold with RPMI1640 medium which is not supplemented with serum (hereinafter, frequently referred to simply as "RPMI-0"). The diluted peripheral blood was added to 10 ml of Ficoll-Paque (manufactured and sold by Pharmacia Biotech AB, Sweden) in a 50 ml centrifuge tube, such that a layer of diluted peripheral blood (upper layer) is formed on a layer of Ficoll-Paque (Ficoll layer) in the tube. Then, the tube was subjected to centrifugation at 400×g for 40 minutes at 20° C. wherein the brake of the centrifuge was set off.

As a result of this centrifugation, a band of peripheral blood mononuclear cells (PBMC) was observed at the interface-between the upper layer and the Ficoll layer, and peripheral blood granulocytes were precipitated together with erythrocytes at the bottom of the centrifuge tube. The band of PMBC was collected using a Pasteur pipette and, then, the upper layer and the Ficoll layer were removed by suction, thereby obtaining precipitated erythrocytes and granulocytes in the form of a mixture thereof.

The recovered PBMC layer was diluted at least two-fold with RPMI-0 and then, centrifuged at 250×g for 5 minutes at 4° C. to thereby collect the cells. The collected cells were used as a "PBMC fraction" in the below-mentioned experiment.

With respect to the mixture of erythrocytes and granulocytes obtained above, RPMI-0 was added thereto so as to obtain a cell suspension having a volume of 10 ml. To the resultant suspension was added 10 ml of a 3% dextran T-500 solution in 0.9% NaCl solution (at room temperature), and the resultant was mixed well. The resultant mixture was allowed to stand at room temperature for 30 minutes, to thereby separate the mixture into an upper layer containing granulocytes and a lower layer containing precipitated erythrocytes. The upper layer containing granulocytes was recovered, and centrifuged in a centrifuge tube at 250×g for 8 minutes at 4° C., to thereby obtain a supernatant and cell pellet. After removing almost all of the supernatant, the cell pellet was well suspended with a small amount of the supernatant remaining in the centrifuge tube. Then, 7 ml of a cold 0.2% NaCl solution was added to and mixed well with the cell suspension to thereby cause hemolysis. 30 seconds after the addition of 0.2% NaCl solution, 7 ml of a cold 1.6% NaCl solution was added to the centrifuge tube and mixed well with the cells contained therein to render the cells isotonic. The resultant mixture was centrifuged at 250×g for 8 minutes at 4° C. to thereby collect cells. The collected cells were used as a "granulocyte fraction" in the below-mentioned experiment.

The purity of each of the PBMC fraction and the granulocyte fraction was measured by means of a flow cytometer. Specifically, the cells (of the PBMC fraction or the granulocyte fraction) were first stained (labeled) as follows. $5 \times 10^4$ to $10 \times 10^4$ cells were placed in a 1.5 ml tube, and the cells were suspended in a 1% BSA solution in PBS (i.e., 1% BSA/PBS). The resultant cell suspension was centrifuged to thereby precipitate a cell fraction. Subsequently, a fluorescence-labeled antibody (diluted twenty-fold with 1% BSA/PBS) was added to the cell fraction so as to effect a reaction between the cells and the fluorescence-labeled antibody at 4° C. for 30 minutes, to thereby stain (label) the cells. Various types of fluorescence-labeled antibodies were used for detecting different types of cells. The antibodies used herein are listed below.

| | |
|---|---|
| For detecting T cells: | FITC (fluorescein isothiocyanate)-labeled anti-human CD3 antibody (clone: HIT3a, catalog number: 30114X, manufactured and sold by PHARMINGEN, U.S.A.) |
| For detecting B cells: | PE (phycoerythrin)-labeled anti-human CD19 antibody (clone: HIB19, catalog number: 30655X, manufactured and sold by PHARMINGEN, U.S.A.) |
| For detecting monocytes: | FITC-labeled anti-human CD14 antibody (clone: M5E2, catalog number: 30544X, manufactured and sold by PHARMINGEN, U.S.A.) |
| For detecting granulocytes: | FITC-labeled anti-CD66b antibody (clone: G10F5, catalog number: 33734X, manufactured and sold by PHARMINGEN, U.S.A.) |

After the reaction, the cells were washed with 1% BSA/PBS and then, passed through a nylon mesh (pore size: 30 μm). Then, the intensity of fluorescence of the resultant cells was measured by means of FACS calibur (a flow cytometer) to determine the purity of the cell fractions.

(2) Preparation of RNA

RNA was extracted from the above-obtained PBMC and granulocytes by the following method.

$5 \times 10^6$ to $10 \times 10^6$ cells were placed in a 1.5 ml tube and washed twice with 0.5 ml of PBS(−). After the washing, the PBS(−) was removed as much as possible. To the resultant washed cells were added 400 μl of a 4 M GITC solution (mixture of 4 M guanidine isothiocyanate, 25 mM sodium citrate (pH 7) and 0.5% sodium N-lauroylsarcosinate) and 2 μl of 2-mercaptoethanol, and the resultant mixture was stirred at room temperature for 10 minutes so as to lyse the cells, thereby obtaining a cell lysate. The genomic DNA released from the cells as a result of the cell lysis was disrupted by means of a 1 ml syringe equipped with a 20G needle. Subsequently, 40 µl of 2 M sodium acetate (pH 4.2), 440 µl of a water-saturated phenol, 120 µl of a chloroform/isoamyl alcohol mixture (chloroform:isoamyl alcohol) =24:1) were successively added to the cell lysate, wherein the additions of the above reagents were individually followed by stirring. The resultant mixture was allowed to stand for 5 minutes in an ice bath. Subsequently, the mixture was centrifuged at 14,000 rpm for 20 minutes at 4° C. by means of a microtube centrifuge. Approximately 300 µl of the uppermost layer of the centrifuged mixture was transferred to another tube and mixed with an equivalent amount (i.e., approximately 300 µl) of 2-propanol. The resultant mixture was allowed to stand at −80° C. for 30 to 60 minutes. Subsequently, the tube was placed in an ice bath to thereby thaw the mixture. The thawed mixture was centrifuged at 14,000 rpm for 30 minutes at 4° C. by means of a microtube centrifuge to thereby obtain a supernatant and precipitate. After removing the supernatant, the precipitate was washed three times with 70% ethanol, thereby obtaining a pelletized crude RNA (i.e., crude RNA pellet), and the crude RNA pellet was air-dried. To the dried RNA pellet was added 10 to 20 µl of sterilized water and then, heated at 65° C. for 1 to 2 minutes in a water bath to thereby dissolve the crude RNA pellet in the water. The resultant crude RNA solution was treated with DNase I (Amplification Grade) (catalog number: 18068-015, manufactured and sold under the brand of GIBCO BRL™, U.S.A.) to thereby decompose the genomic DNA remaining in the crude RNA solution. The resultant RNA solution was subjected to purification by phenol/chloroform extraction and subsequent ethanol precipitation to thereby precipitate a purified RNA. The resultant purified RNA precipitate was dissolved in sterilized water and used as an RNA in item (3) below.

(3) RT-PCR Method

From 1 to 5 µg of the above-obtained RNA, cDNA was synthesized by a reverse transcription reaction using SUPERSCRIPT™ II RNase H-Reverse Transcriptase (catalog number: 18064-014, manufactured and sold under the brand of GIBCO BRL™, U.S.A.) in accordance with the protocol attached thereto. In this Example, the amount of the mRNA encoding the C5L2 protein was determined in terms of the ratio of the expression of a gene encoding the C5L2 protein, based on the expression of a gene encoding the G3PDH protein. For this purpose, the cDNA corresponding to the gene encoding C5L2 protein and the cDNA corresponding to the gene encoding G3PDH protein were both amplified by PCR.

PCR was conducted using GeneAmp™ PCR Core Reagents (manufactured and sold by The Perkin-Elmer Corporation, U.S.A.) in accordance with the protocol attached thereto. To 21.3 µl of a cDNA solution (containing cDNA in an amount corresponding to 15 ng of RNA) were added 3 µl of 10×PCR buffer, 2.4 µl of 25 mM MgCl$_2$, 0.6 µl of each of 10 mM DATP, dGTP, dCTP and dTTP, 0.3 µl of each of 20 µM 5'-primer and 3'-primer, 0.15 µl of TaqStart™ Antibody (manufactured and sold by CLONTECH laboratories Inc., U.S.A.) and 0.15 µl of AmpliTaq™ DNA Polymerase, and the resultant was mixed well. For amplifying the C5L2 gene, the oligonucleotides respectively having the nucleotide sequences of SEQ ID NOs:9 and 10 were employed as the primers. On the other hand, for amplifying the G3PDH gene, the oligonucleotides respectively having the nucleotide sequences of SEQ ID NOs:11 and 12 were employed as the primers. The above-obtained mixture was subjected to PCR using TaKaRa PCR Thermal Cycler 480. Specifically, the template DNA was first denatured (i.e., the dsDNA was melted into ssDNA) by heating at 94° C. for 2 minutes. Then, 30 cycles of PCR were conducted, wherein each cycle was conducted under the following conditions: 45 seconds at 94° C., 45 seconds at 60° C. and 2 minutes at 72° C. After the last cycle, the elongation reaction was effected for 7 minutes at 72° C. The resultant reaction mixture was cooled to 4° C. to thereby complete the reaction. 10 µl of the reaction mixture was electrophoresed on 2% agarose gel. The resultant electropherogram was converted to digital data by means of Gel Print 2000i/VGA (manufactured and sold by Bio Image, U.S.A.), and the converted data was analyzed with a computer software Basic Quantifier (manufactured and sold by Nippon Bio Image Limited, Japan), so as to determine the amount of the PCR product (i.e., the DNA amplified by PCR). The amount of the PCR product corresponding to the C5L2 gene expression was calculated in terms of the ratio of the amount of the PCR product corresponding to the C5L2 gene expression based on the amount of the PCR product corresponding to the G3PDH gene expression.

Each of the PCR of the cDNA corresponding to the C5L2 gene and the PCR of the cDNA corresponding to the G3PDH gene was conducted twice, and the mean amounts of the PCR products were used for the calculation.

(4) Analysis of Healthy Persons

In accordance with the methods described in items (1) to (3) above, the ratios of the expression of the C5L2 gene in PBMC (peripheral blood mononuclear cells) and granulocytes sampled from 8 healthy volunteers were determined.

As a result of the determination of the purity of cell fractions by means of a flow cytometer, it was found that the ratio of CD66b-positive cells in the granulocyte fraction was 90.5±3.2% (mean±S.E.), and that the ratio of CD66b-positive cells in the PBMC fraction was 4.1±0.9%.

The ratio of the expression of C5L2 gene in the granulocytes was as high as 73.4±17.8%, whereas the ratio of the expression of C5L2 gene in PBMC was only 0.5±0.5%. These results clearly show that the C5L2 gene is expressed mainly in granulocytes ($p \leq 0.01$). The results are shown in Table 1.

TABLE 1

Ratios of expression of C5L2 gene in PBMC fraction and granulocyte fraction, each obtained from peripheral blood of healthy volunteers

|  | PBMC fraction | Granulocyte fraction |
| --- | --- | --- |
| Ratio of expression of C5L2 gene[a] | 0.5 ± 0.5 | 73.4 ± 17.8 |
| Ratio of CD66b-positive cells[b] | 4.1 ± 0.9 | 90.5 ± 3.2 |

Notes: Values are mean ± S.E.
[a] % based on the expression of G3PDH gene
[b] Analysis by FACS (%)

(5) Change with Time in Ratio of the Expression of C5L2 Gene After the Collection of Blood How the ratio of the expression of C5L2 gene changes with time after the collection of blood was determined as follows.

With respect to the blood sampled from 8 healthy volunteers, the expression of C5L2 gene in granulocytes obtained from blood immediately after the blood collection (hereinafter, frequently referred to as "fresh blood") was compared with that in granulocytes obtained from blood after allowing the blood to stand overnight (hereinafter, frequently referred to as "stored blood").

The ratio of the expression of C5L2 gene in granulocytes obtained from fresh blood was as high as 73.4±17.8%, whereas the ratio of the expression of C5L2 gene in granulocytes obtained from stored blood was only 10.8±3.1% (wherein each ratio of the expression is a value based on the expression of G3PDH). These results clearly show that the expression of C5L2 gene is decreased with the lapse of time after the blood collect ion ($p \leq 0.01$). The results are shown in Table 3 below.

Further, with respect to 3 healthy volunteers, granulocyte fractions were obtained from peripheral blood immediately after the blood collection, 6 hours after the blood collection and 24 hours after the blood collection. The ratio of the expression of C5L2 gene in each of the granulocyte fractions was measured.

As a result, it was found that the mean ratio of the expression of C5L2 gene in the granulocytes obtained from peripheral blood immediately after the collection of the blood was 71.7%. The mean ratio of the expression of C5L2 gene in the granulocytes obtained from peripheral blood 6 hours after the blood collection was 31.1%. The mean ratio of the expression of C5L2 gene in the granulocytes obtained from peripheral blood 24 hours after the blood collection was 10.6%.

Figure 2:
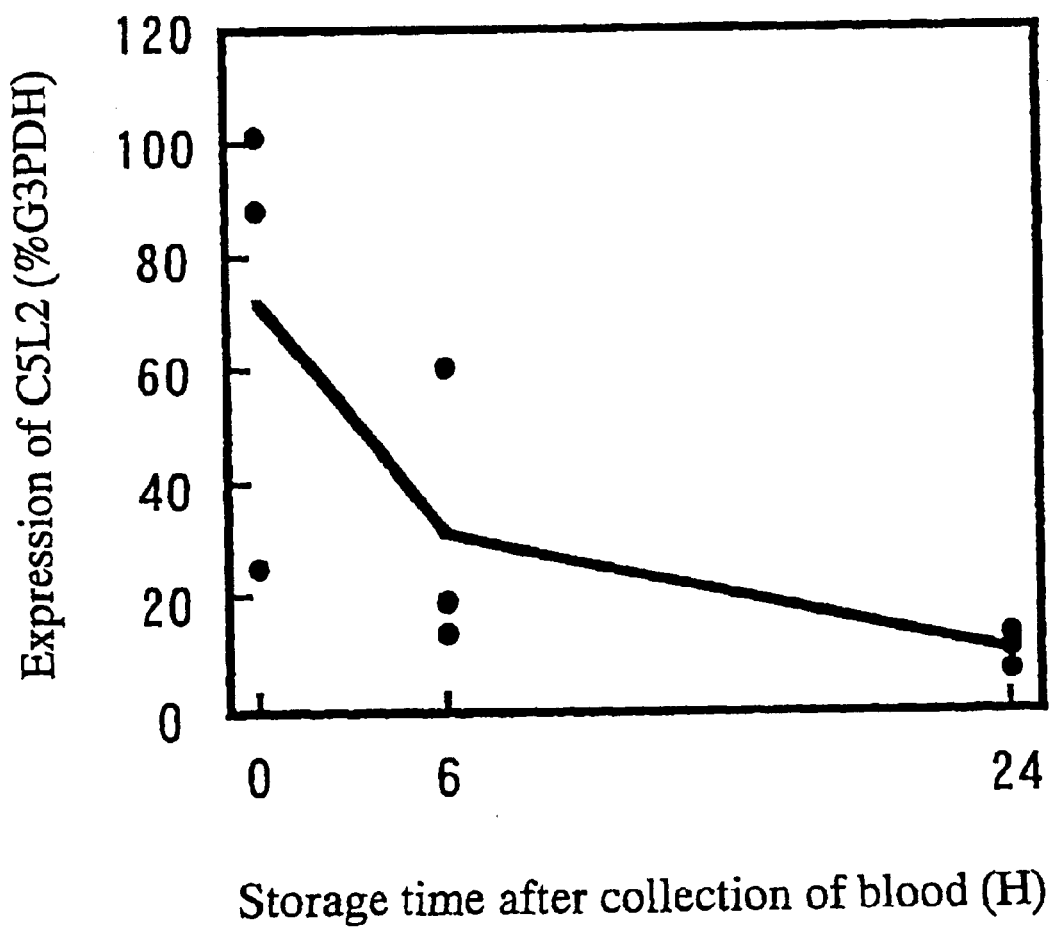
FIG. 2 is a graph showing how the expression of C5L2 gene in granulocytes obtained from peripheral blood of healthy volunteers changes with time during the storage at room temperature, wherein the ordinate shows the expression of C5L2 and the abscissa shows the storage time after the collection of the blood, and wherein each dot represents an individual determined value of the expression of C5L2 gene, and the line connects the average values of the expression respectively obtained at the measuring points in time.

From these results, it was found that the ratio of the expression of the C5L2 gene decreases rapidly during the period of time of 0 to 6 hours after the collection of the blood, and then decreases gradually, wherein the decrease in ratio of the expression continues for 24 hours after the collection of the blood. The results are shown in FIG. 2.

(6) Analysis of RA Patients

A PBMC fraction and a granulocyte fraction were obtained from fresh blood collected from 8 RA patients, and the ratio of the expression of C5L2 gene in PBMC was compared with that in granulocytes. As a result, it was found that almost no expression of C5L2 gene was observed in the PBMC fraction (0.0±0.0%), and that the expression of C5L2 gene was observed only in the granulocyte fraction (44.7±4.7%). That is, it was found that with respect to RA patients, as in the case of healthy persons, the ratio of the C5L2 expression was significantly high in the granulocyte fraction ($p \leq 0.01$). The ratio of CD66b-positive cells in the PBMC fraction was 3.3±2.2%, whereas the ratio of CD66b-positive cells in the granulocyte fraction was 80.9±5.8%. The results are shown in Table 2.

Next, the ratio of the expression of C5L2 gene was determined with respect to granulocyte fractions respectively obtained from the fresh blood of 8 RA patients and the stored blood of 12 RA patients, and the results were compared with the ratios of the C5L2 gene expression in the fresh blood and the stored blood of 8 healthy volunteers. As a result, is was found that the ratio of the expression of C5L2 gene in the granulocyte fraction obtained from the fresh blood of RA patients was 44.7±4.7%, and the ratio of the expression of C5L2 gene in the granulocyte fraction obtained from the stored blood of RA patients was 42.8±6.9% (wherein each ratio of the expression is a value based on the expression of G3PDH).

These results clearly show that, unlike the ratio a of the expression of C5L2 gene in the granulocyte fraction obtained from healthy persons, the ratio of the expression of C5L2 gene in the granulocyte fraction obtained from RA patients does not decrease with the lapse of time, and the ratio of C5L2 gene expression in granulocytes is maintained.

With respect to healthy persons, the ratio of the expression of the C5L2 gene in the granulocyte fraction obtained from the stored blood was 10.8±3.1%; whereas, with respect to RA patients, the ratio of the expression of the C5L2 gene in the granulocyte fraction obtained from the stored blood was 42.8±6.9%. Thus, it was found that the ratio of the expression of the C5L2 gene in the stored blood of RA patients was significantly high, as compared to that of healthy persons ($p \leq 0.001$). The results are shown in Table 3.

TABLE 2

Ratios of expression of C5L2 gene in PBMC fraction and granulocyte fraction, each obtained from peripheral blood of RA patients

|  | PBMC fraction | Granulocyte fraction |
|---|---|---|
| Ratio of expression of C5L2 gene[a] | 0.0 ± 0.0 | 44.7 ± 4.7 |
| Ratio of CD66b-positive cells[b] | 3.3 ± 2.2 | 80.9 ± 5.8 |

Notes: Values are mean ± S.E.
[a]% based on the expression of G3PDH gene
[b]Analysis by FACS (%)

TABLE 3

How the ratios of the expression of C5L2 gene change with time (during storage) in granulocyte fractions respectively obtained from peripheral blood of healthy persons and peripheral blood of RA patients

|  | Fresh blood | Stored blood |
|---|---|---|
| Granulocyte fraction obtained from healthy persons | 73.4 ± 17.8 | 10.8 ± 3.1 |
| Granulocyte fraction obtained from RA patients | 44.7 ± 4.7 | 42.8 ± 6.9 |

Notes: Ratio (%) of C5L2 expression is a value based on the expression of G3PDH gene.
Values are mean ± S.E.

Figure 3:
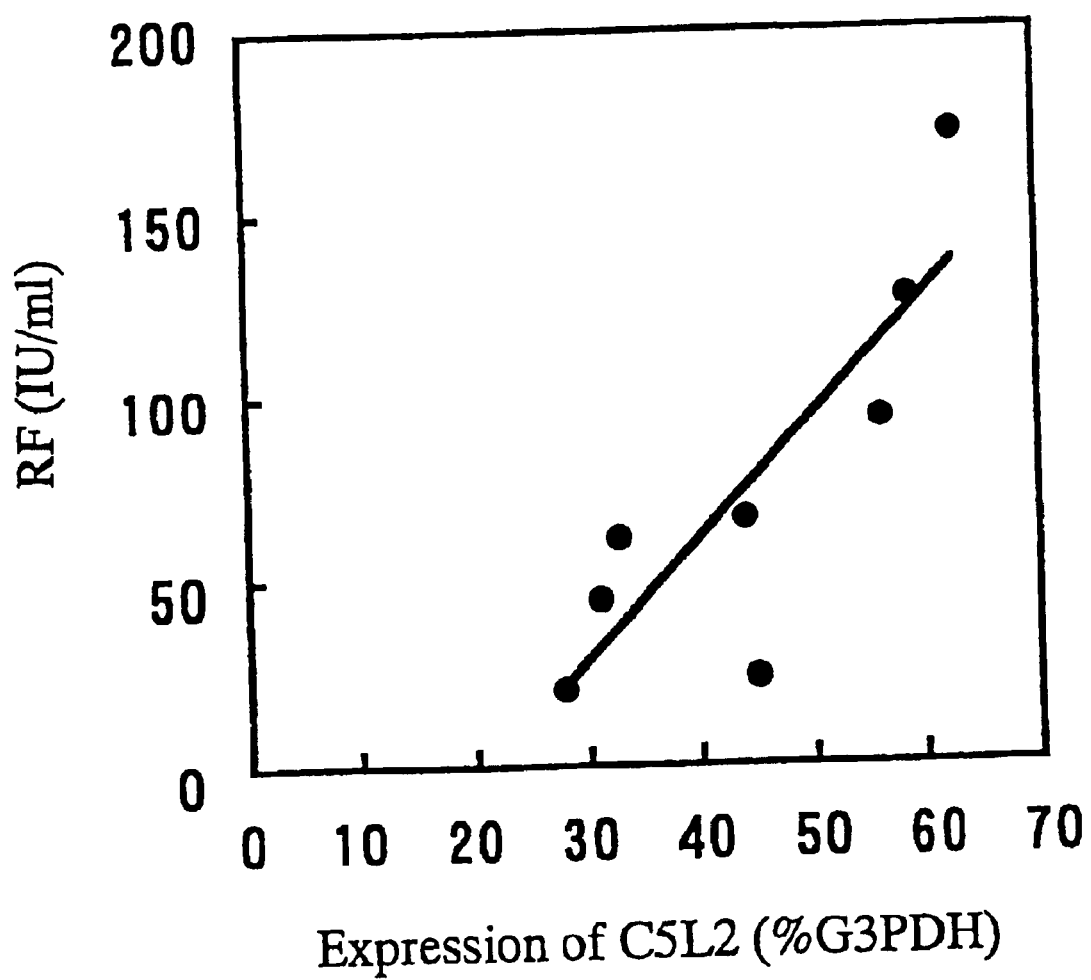
FIG. 3 is a graph (scatter diagram) showing the relationship between the expression of C5L2 gene in granulocytes obtained from fresh blood of RA patients and the amount of the rheumatoid factor present in the fresh blood, wherein the ordinate shows the amount of the rheumatoid factor and the abscissa shows the expression of C5L2 gene.

Further, a significant positive correlation was observed between the expression of C5L2 gene in fresh blood of RA patients and the expression of rheumatoid factor (correlation coefficient R=0.846, $p \leq 0.01$). This clearly shows that the expression of C5L2 gene is useful for the diagnosis of rheumatism. The results are shown in FIG. 3.

INDUSTRIAL APPLICABILITY

By the use of the novel human seven-pass transmembrane receptor protein and the DNA encoding the same which are provided according to the present invention, it has become possible to screen a substance which can be used for treating or preventing diseases mediated by the functions of dendritic cells, and to provide a method and a reagent for the diagnosis of such diseases. Further, by the method of the present invention for the diagnosis of an inflammatory disease, which comprises determining the amount of the seven-pass transmembrane receptor protein expressed in human leukocytes, it has become possible not only to perform the diagnosis of an inflammatory disease speedily, but also to realize the early diagnosis of a disease, such as rheumatism, which has conventionally been difficult to diagnose at an early stage thereof.

SEQUENCE LISTING

<160> NUMBER OF SEQ ID NOS: 19

<210> SEQ ID NO 1
<211> LENGTH: 1014
<212> TYPE: DNA
<213> ORGANISM: Homo sapiens
<220> FEATURE:
<221> NAME/KEY: CDS
<222> LOCATION: (1)..(1011)

<400> SEQUENCE: 1

```
atg ggg aac gat tct gtc agc tac gag tat ggg gat tac agc gac ctc      48
Met Gly Asn Asp Ser Val Ser Tyr Glu Tyr Gly Asp Tyr Ser Asp Leu
 1               5                  10                  15 tcg gac cgc cct gtg gac tgc ctg gat ggc gcc tgc ctg gcc atc gac      96
Ser Asp Arg Pro Val Asp Cys Leu Asp Gly Ala Cys Leu Ala Ile Asp
             20                  25                  30 ccg ctg cgc gtg gcc ccg ctc cca ctg tat gcc gcc atc ttc ctg gtg     144
Pro Leu Arg Val Ala Pro Leu Pro Leu Tyr Ala Ala Ile Phe Leu Val
         35                  40                  45 ggg gtg ccg ggc aat gcc atg gtg gcc tgg gtg gct ggg aag gtg gcc     192
Gly Val Pro Gly Asn Ala Met Val Ala Trp Val Ala Gly Lys Val Ala
     50                  55                  60 cgc cgg agg gtg ggt gcc acc tgg ttg ctc cac ctg gcc gtg gcg gat     240
Arg Arg Arg Val Gly Ala Thr Trp Leu Leu His Leu Ala Val Ala Asp
 65                  70                  75                  80 ttg ctg tgc tgt ttg tct ctg ccc atc ctg gca gtg ccc att gcc cgt     288
Leu Leu Cys Cys Leu Ser Leu Pro Ile Leu Ala Val Pro Ile Ala Arg
                 85                  90                  95 gga ggc cac tgg ccg tat ggt gca gtg ggc tgt cgg gcg ctg ccc tcc     336
Gly Gly His Trp Pro Tyr Gly Ala Val Gly Cys Arg Ala Leu Pro Ser
            100                 105                 110 atc atc ctg ctg acc atg tat gcc agc gtc ctg ctc ctg gca gct ctc     384
Ile Ile Leu Leu Thr Met Tyr Ala Ser Val Leu Leu Leu Ala Ala Leu
        115                 120                 125 agt gcc gac ctc tgc ttc ctg gct ctc ggg cct gcc tgg tgg tct acg     432
Ser Ala Asp Leu Cys Phe Leu Ala Leu Gly Pro Ala Trp Trp Ser Thr
    130                 135                 140 gtt cag cgg gcg tgc ggg gtg cag gtg gcc tgt ggg gca gcc tgg aca     480
Val Gln Arg Ala Cys Gly Val Gln Val Ala Cys Gly Ala Ala Trp Thr
145                 150                 155                 160 ctg gcc ttg ctc ctc acc gtg ccc tcc gcc atc tac cgc cgg ctg cac     528
Leu Ala Leu Leu Leu Thr Val Pro Ser Ala Ile Tyr Arg Arg Leu His
                165                 170                 175 cag gag cac ttc cca gcc cgg ctg cag tgt gtg gtg gac tac ggc ggc     576
Gln Glu His Phe Pro Ala Arg Leu Gln Cys Val Val Asp Tyr Gly Gly
            180                 185                 190 tcc tcc agc acc gag aat gcg gtg act gcc atc cgg ttt ctt ttt ggc     624
Ser Ser Ser Thr Glu Asn Ala Val Thr Ala Ile Arg Phe Leu Phe Gly
        195                 200                 205 ttc ctg ggg ccc ctg gtg gcc gtg gcc agc tgc cac agt gcc ctc ctg     672
Phe Leu Gly Pro Leu Val Ala Val Ala Ser Cys His Ser Ala Leu Leu
    210                 215                 220 tgc tgg gca gcc cga cgc tgc cgg ccg ctg ggc aca gcc att gtg gtg     720
Cys Trp Ala Ala Arg Arg Cys Arg Pro Leu Gly Thr Ala Ile Val Val
225                 230                 235                 240 ggg ttt ttt gtc tgc tgg gca ccc tac cac ctg ctg ggg ctg gtg ctc     768
Gly Phe Phe Val Cys Trp Ala Pro Tyr His Leu Leu Gly Leu Val Leu
                245                 250                 255
```

```
act gtg gcg gcc ccg aac tcc gca ctc ctg gcc agg gcc ctg cgg gct      816
Thr Val Ala Ala Pro Asn Ser Ala Leu Leu Ala Arg Ala Leu Arg Ala
        260                 265                 270 gaa ccc ctc atc gtg ggc ctt gcc ctc gct cac agc tgc ctc aat ccc      864
Glu Pro Leu Ile Val Gly Leu Ala Leu Ala His Ser Cys Leu Asn Pro
    275                 280                 285 atg ctc ttc ctg tat ttt ggg agg gct caa ctc cgc cgg tca ctg cca      912
Met Leu Phe Leu Tyr Phe Gly Arg Ala Gln Leu Arg Arg Ser Leu Pro
290                 295                 300 gct gcc tgt cac tgg gcc ctg agg gag tcc cag ggc cag gac gaa agt      960
Ala Ala Cys His Trp Ala Leu Arg Glu Ser Gln Gly Gln Asp Glu Ser
305                 310                 315                 320 gtg gac agc aag aaa tcc acc agc cat gac ctg gtc tcg gag atg gag     1008
Val Asp Ser Lys Lys Ser Thr Ser His Asp Leu Val Ser Glu Met Glu
                325                 330                 335 gtg tag                                                              1014
Val

<210> SEQ ID NO 2
<211> LENGTH: 337
<212> TYPE: PRT
<213> ORGANISM: Homo sapiens

<400> SEQUENCE: 2

Met Gly Asn Asp Ser Val Ser Tyr Glu Tyr Gly Asp Tyr Ser Asp Leu
 1               5                  10                  15

Ser Asp Arg Pro Val Asp Cys Leu Asp Gly Ala Cys Leu Ala Ile Asp
            20                  25                  30

Pro Leu Arg Val Ala Pro Leu Pro Leu Tyr Ala Ala Ile Phe Leu Val
        35                  40                  45

Gly Val Pro Gly Asn Ala Met Val Ala Trp Val Ala Gly Lys Val Ala
    50                  55                  60

Arg Arg Arg Val Gly Ala Thr Trp Leu His Leu Ala Val Ala Asp
 65                 70                  75                  80

Leu Leu Cys Cys Leu Ser Leu Pro Ile Leu Ala Val Pro Ile Ala Arg
                85                  90                  95

Gly Gly His Trp Pro Tyr Gly Ala Val Gly Cys Arg Ala Leu Pro Ser
            100                 105                 110

Ile Ile Leu Leu Thr Met Tyr Ala Ser Val Leu Leu Leu Ala Ala Leu
        115                 120                 125

Ser Ala Asp Leu Cys Phe Leu Ala Leu Gly Pro Ala Trp Trp Ser Thr
    130                 135                 140

Val Gln Arg Ala Cys Gly Val Gln Val Ala Cys Gly Ala Ala Trp Thr
145                 150                 155                 160

Leu Ala Leu Leu Leu Thr Val Pro Ser Ala Ile Tyr Arg Arg Leu His
                165                 170                 175

Gln Glu His Phe Pro Ala Arg Leu Gln Cys Val Val Asp Tyr Gly Gly
            180                 185                 190

Ser Ser Ser Thr Glu Asn Ala Val Thr Ala Ile Arg Phe Leu Phe Gly
        195                 200                 205

Phe Leu Gly Pro Leu Val Ala Val Ala Ser Cys His Ser Ala Leu Leu
    210                 215                 220

Cys Trp Ala Ala Arg Arg Cys Arg Pro Leu Gly Thr Ala Ile Val Val
225                 230                 235                 240

Gly Phe Phe Val Cys Trp Ala Pro Tyr His Leu Leu Gly Leu Val Leu
                245                 250                 255
```

```
Thr Val Ala Ala Pro Asn Ser Ala Leu Leu Ala Arg Ala Leu Arg Ala
            260                 265                 270
Glu Pro Leu Ile Val Gly Leu Ala Leu Ala His Ser Cys Leu Asn Pro
        275                 280                 285
Met Leu Phe Leu Tyr Phe Gly Arg Ala Gln Leu Arg Arg Ser Leu Pro
    290                 295                 300
Ala Ala Cys His Trp Ala Leu Arg Glu Ser Gln Gly Gln Asp Glu Ser
305                 310                 315                 320
Val Asp Ser Lys Lys Ser Thr Ser His Asp Leu Val Ser Glu Met Glu
                325                 330                 335
Val

<210> SEQ ID NO 3
<211> LENGTH: 1287
<212> TYPE: DNA
<213> ORGANISM: Homo sapiens

<400> SEQUENCE: 3
cctgtgtgcc acgtgctgga caaatcttaa ctcctcaagg actcccaaaa ccagagacac      60
caggagcctg aatggggaac gattctgtca gctacgagta tggggattac agcgacctct     120
cggaccgccc tgtggactgc ctggatggcg cctgcctggc catcgacccg ctgcgcgtgg     180
ccccgctccc actgtatgcc gccatcttcc tggtgggggt gccgggcaat gccatggtgg     240
cctgggtggc tgggaaggtg gcccgccgga gggtgggtgc cacctggttg ctccacctgg     300
ccgtggcgga tttgctgtgc tgtttgtctc tgcccatcct ggcagtgccc attgcccgtg     360
gaggccactg gccgtatggt gcagtgggct gtcgggcgct gccctccatc atcctgctga     420
ccatgtatgc cagcgtcctg ctcctggcag ctctcagtgc cgacctctgc ttcctggctc     480
tcgggcctgc ctggtggtct acggttcagc gggcgtgcgg ggtgcaggtg gcctgtgggg     540
cagcctggac actggccttg ctgctcaccg tgccctccgc catctaccgc cggctgcacc     600
aggagcactt cccagcccgg ctgcagtgtg tggtggacta cggcggctcc tccagcaccg     660
agaatgcggt gactgccatc cggtttcttt ttggcttcct ggggcccctg gtggccgtgg     720
ccagctgcca cagtgccctc ctgtgctggg cagcccgacg ctgccggccg ctgggcacag     780
ccattgtggt ggggtttttt gtctgctggg cacctactcc cctgctgggg ctggtgctca     840
ctgtggcggc cccgaactcc gcactcctgg ccagggccct gcgggctgaa cccctcatcg     900
tgggccttgc cctcgctcac agctgcctca tcccatgct cttcctgtat tttgggaggg     960
ctcaactccg ccggtcactg ccagctgcct gtcactgggc cctgagggag tcccagggcc    1020
aggacgaaag tgtggacagc aagaaatcca ccagccatga cctggtctcg agatggaggt    1080
gtaggctgg agagacattg tgggtgtgta tcttcttatc tcatttcaca agactggctt    1140
caggcatagc tggatccagg agctcaatga tgtcttcatt ttattccttc cttcattcaa    1200
cagatatcca tcatgcactt gctatgtgca aggccttttt aggcactaga gatatagcag    1260
tgaccaaaac agacacaaat cctgccc                                         1287

<210> SEQ ID NO 4
<211> LENGTH: 1287
<212> TYPE: DNA
<213> ORGANISM: Homo sapiens

<400> SEQUENCE: 4
gggcaggatt tgtgtctgtt ttggtcactg ctatatctct agtgcctaaa aaggccttgc      60
```

```
acatagcaag tgcatgatgg atatctgttg aatgaaggaa ggaataaaat gaagacatca      120
ttgagctcct ggatccagct atgcctgaag ccagtcttgt gaaatgagat aagaagatac      180
acacccacaa tgtctctcca gcctacacct ccatctccga gaccaggtca tggctggtgg      240
atttcttgct gtccacactt tcgtcctggc cctgggactc cctcagggcc cagtgacagg      300
cagctggcag tgaccggcgg agttgagccc tcccaaaata caggaagagc atgggattga      360
ggcagctgtg agcgagggca aggcccacga tgaggggttc agcccgcagg gccctggcca      420
ggagtgcgga gttcggggcc gccacagtga gcaccagccc cagcaggtgg tagggtgccc      480
agcagacaaa aaaccccacc acaatggctg tgcccagcgg ccggcagcgt cgggctgccc      540
agcacaggag ggcactgtgg cagctggcca cggccaccag gggcccaggg aagccaaaaa      600
gaaaccggat ggcagtcacc gcattctcgg tgctggagga gccgccgtag tccaccacac      660
actgcagccg ggctgggaag tgctcctggt gcagccggcg gtagatggcg gagggcacgg      720
tgagcagcaa ggccagtgtc caggctgccc cacaggccac ctgcaccccg cacgcccgct      780
gaaccgtaga ccaccaggca ggcccgagag ccaggaagca gaggtcggca ctgagagctg      840
ccaggagcag gacgctggca tacatggtca gcaggatgat ggagggcagc gcccgacagc      900
ccactgcacc atacggccag tggcctccac gggcaatggg cactgccagg atgggcagag      960
acaaacagca cagcaaatcc gccacggcca ggtggagcaa ccaggtggca cccaccctcc     1020
ggcgggccac cttcccagcc acccaggcca ccatggcatt gcccggcacc cccaccagga     1080
agatggcggc atacagtggg agcggggcca cgcgcagcgg gtcgatggcc aggcaggcgc     1140
catccaggca gtccacaggg cggtccgaga ggtcgctgta atccccatac tcgtagctga     1200
cagaatcgtt ccccattcag gctcctggtg tctctggttt tgggagtcct tgaggagtta     1260
agatttgtcc agcacgtggc acacagg                                         1287

<210> SEQ ID NO 5
<211> LENGTH: 30
<212> TYPE: DNA
<213> ORGANISM: Artificial Sequence
<220> FEATURE:
<223> OTHER INFORMATION: Degenerative PCR primer designed based on the
      seq of conventional 7-pass transmembrane receptor proteins which
      are considered to participate in the proliferation of melanoma
<220> FEATURE:
<221> NAME/KEY: modified_base
<222> LOCATION: (18)
<223> OTHER INFORMATION: i
<220> FEATURE:
<221> NAME/KEY: modified_base
<222> LOCATION: (22)
<223> OTHER INFORMATION: i
<220> FEATURE:
<221> NAME/KEY: modified_base
<222> LOCATION: (24)
<223> OTHER INFORMATION: i

<400> SEQUENCE: 5
atcttaagct tgaacctngc cntngcdgac                                       30

<210> SEQ ID NO 6
<211> LENGTH: 33
<212> TYPE: DNA
<213> ORGANISM: Artificial Sequence
<220> FEATURE:
<223> OTHER INFORMATION: Degenerative PCR primer designed based on the
      seq of conventional 7-pass transmembrane receptor proteins which
      are considered to participate in the proliferation of melanoma
<220> FEATURE:
<221> NAME/KEY: misc_difference
```

```
<222> LOCATION: (21)
<223> OTHER INFORMATION: a, g, c or t
<220> FEATURE:
<221> NAME/KEY: modified_base
<222> LOCATION: (22)
<223> OTHER INFORMATION: i
<220> FEATURE:
<221> NAME/KEY: modified_base
<222> LOCATION: (28)
<223> OTHER INFORMATION: i

<400> SEQUENCE: 6
cccaacgaat tcrtagatsa nnggrttnav rca                          33

<210> SEQ ID NO 7
<211> LENGTH: 32
<212> TYPE: DNA
<213> ORGANISM: Artificial Sequence
<220> FEATURE:
<223> OTHER INFORMATION: Synthetic primer used for constructing the
      recombinant DNA containing C5L2 gene; primer has a seq obtained by
      adding spacer gggg and HindIII site aagctt to the 5 prime-end of a
      22-nucleotide seq corresponding to the 1st (a) to 22nd (t) of SEQ
      ID NO:1

<400> SEQUENCE: 7
ggggaagctt atggggaacg attctgtcag ct                           32

<210> SEQ ID NO 8
<211> LENGTH: 30
<212> TYPE: DNA
<213> ORGANISM: Artificial Sequence
<220> FEATURE:
<223> OTHER INFORMATION: Synthetic primer used for constructing the
      recombinant DNA containing C5L2 gene; primer has a seq obtained by
      adding spacer ggga and SacII site ccgcgg to the 5 prime-end of a
      20-nucleotide seq corresponding to the 206th (c) to 225th (a) of
      SEQ ID NO:4

<400> SEQUENCE: 8
gggaccgcgg cacctccatc tccgagacca                              30

<210> SEQ ID NO 9
<211> LENGTH: 26
<212> TYPE: DNA
<213> ORGANISM: Artificial Sequence
<220> FEATURE:
<223> OTHER INFORMATION: Synthetic primer used in RT-PCR performed for
      amplifying C5L2 gene

<400> SEQUENCE: 9
atcatcctgc tgaccatgta tgccag                                  26

<210> SEQ ID NO 10
<211> LENGTH: 25
<212> TYPE: DNA
<213> ORGANISM: Artificial Sequence
<220> FEATURE:
<223> OTHER INFORMATION: Synthetic primer used in RT-PCR performed for
      amplifying C5L2 gene

<400> SEQUENCE: 10
aaccggatgg cagtcaccgc attct                                   25

<210> SEQ ID NO 11
<211> LENGTH: 26
<212> TYPE: DNA
<213> ORGANISM: Artificial Sequence
<220> FEATURE:
```

<223> OTHER INFORMATION: Synthetic primer used in RT-PCR performed for
      amplifying G3PDH (glyceraldehyde 3-phosphate dehydrogenase) gene

<400> SEQUENCE: 11
tgaaggtcgg agtcaacgga tttggt                                            26

<210> SEQ ID NO 12
<211> LENGTH: 24
<212> TYPE: DNA
<213> ORGANISM: Artificial Sequence
<220> FEATURE:
<223> OTHER INFORMATION: Synthetic primer used in RT-PCR performed for
      amplifying G3PDH (glyceraldehyde 3-phosphate dehydrogenase) gene

<400> SEQUENCE: 12
catgtgggcc atgaggtcca ccac                                              24

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide tag

<400> SEQUENCE: 13

Met Asp Tyr Lys Asp Asp Asp Asp Lys
  1               5

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide tag

<400> SEQUENCE: 14

Met Ala Ser Met Thr Gly Gly Gln Gln Met Gly
  1               5                  10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide tag

<400> SEQUENCE: 15

Ser Gln Pro Glu Leu Ala Pro Glu Asp Pro Glu Asp
  1               5                  10

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide tag

<400> SEQUENCE: 16

Lys Glu Thr Ala Ala Ala Lys Phe Glu Arg Gln His Met Asp Ser
  1               5                  10                  15

<210> SEQ ID NO 17
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide tag

<400> SEQUENCE: 17

Glu Gln Lys Leu Ile Ser Glu Glu Asp Leu
 1               5                  10

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide tag

<400> SEQUENCE: 18

His His His His His His His His
 1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide tag

<400> SEQUENCE: 19

Tyr Pro Tyr Asp Val Pro Asp Tyr Ala
 1               5
```

What is claimed is:

1. A purified human seven-pass transmembrane receptor protein having the amino acid sequence of SEQ ID NO:2.

2. A purified peptide which is a fragmentary sequence selected from the group consisting of the 6th to 32nd amino acid residues of SEQ ID NO:2, the 1st to 23rd amino acid residues of SEQ ID NO:2, the 1st to 35th amino acid residues of SEQ ID NO:2, the 96th to 108th amino acid residues of SEQ ID NO:2, and the 172nd to 198th amino acid residues of SEQ ID NO:2.

3. An isolated DNA encoding the seven-pass transmembrane receptor protein of claim 1.

4. The isolated DNA according to claim 3, having the nucleotide sequence of SEQ ID NO:1.

5. A seven-pass transmembrane receptor protein prepared by a process which comprises:

transforming host cells with an expression vector comprising the DNA of claim 3 or 4 under conditions suitable to express said DNA and to produce a protein on the cell surface of said transformed cells.

* * * * *